(12) United States Patent
Gordon

(10) Patent No.: US 11,504,241 B2
(45) Date of Patent: *Nov. 22, 2022

(54) PATIENT-SPECIFIC CRANIOFACIAL IMPLANTS

(71) Applicant: Plastic Surgery LLC, Cockeysville, MD (US)

(72) Inventor: Chad Gordon, Cockeysville, MD (US)

(73) Assignee: Plastic Surgery LLC, Cockeysville, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 17/712,311

(22) Filed: Apr. 4, 2022

(65) Prior Publication Data

US 2022/0218486 A1 Jul. 14, 2022

Related U.S. Application Data

(60) Continuation of application No. 16/830,748, filed on Mar. 26, 2020, now Pat. No. 11,304,808, which is a
(Continued)

(51) Int. Cl.
*A61F 2/28* (2006.01)
*A61F 2/00* (2006.01)
*A61F 2/30* (2006.01)

(52) U.S. Cl.
CPC .......... *A61F 2/2875* (2013.01); *A61F 2/0059* (2013.01); *A61F 2/28* (2013.01);
(Continued)

(58) Field of Classification Search
CPC ........ A61F 2/28; A61F 2/2875; A61F 2/0059; A61F 2/30942; A61F 2002/2878;
(Continued)

(56) References Cited

U.S. PATENT DOCUMENTS 4,436,684 A 3/1984 White
4,990,160 A 2/1991 Terino
(Continued)

FOREIGN PATENT DOCUMENTS

EP 1957128 A2 8/2008
JP 2001092950 A 4/2001
(Continued)

OTHER PUBLICATIONS

Synthes CMF Customized Surgical Solutions—PSI Ordering Process, ® 2006-2012.
(Continued)

*Primary Examiner* — Dinah Baria
(74) *Attorney, Agent, or Firm* — Maier & Maier, PLLC

(57) ABSTRACT

Patient-specific craniofacial implants structured for filling bone voids or planned bone voids in the cranium and face as well as for simultaneously providing soft tissue reconstruction and/or augmentation for improved aesthetic symmetry and appearance of face and skull. Pterional or temporal voids or defects generally result from a chronic skull or lateral facial deformity along with a compromised temporalis muscle or soft tissue distortion from previous surgery. When muscle and fat atrophy occurs in the pterion or temporal face, temporal hollowing deformity generally results where there would be soft tissue but for the atrophy. The patient-specific craniofacial implants with dual-purpose herein are configured to have an augmented region adjacent the temporal region of the face and cranium in order to prevent and/or correct any such temporal hollowing deformity and to utilize this newfound space to strategically embed implantable neurotechnologies for improved outcomes.

2 Claims, 13 Drawing Sheets

Related U.S. Application Data continuation of application No. 16/377,455, filed on Apr. 8, 2019, now Pat. No. 10,639,158, which is a continuation-in-part of application No. 16/139,542, filed on Sep. 24, 2018, now Pat. No. 10,918,485, which is a continuation of application No. 14/958,161, filed on Dec. 3, 2015, now Pat. No. 10,080,662, which is a division of application No. 13/963,225, filed on Aug. 9, 2013, now Pat. No. 9,216,084.

(52) U.S. Cl.
CPC .  *A61F 2/30942* (2013.01); *A61F 2002/30948* (2013.01); *A61F 2002/30952* (2013.01); *A61F 2240/002* (2013.01)

(58) Field of Classification Search
CPC .... A61F 2002/2882; A61F 2002/30948; A61F 2002/30952; A61F 2240/002
See application file for complete search history.

(56) References Cited

U.S. PATENT DOCUMENTS

| | | | |
|---|---|---|---|
| 5,195,951 | A | 3/1993 | Giampapa |
| 5,380,329 | A | 1/1995 | Elia et al. |
| 5,391,181 | A | 2/1995 | Johnson et al. |
| 5,421,831 | A | 6/1995 | Giampapa |
| 5,514,179 | A | 5/1996 | Brennan |
| 5,658,516 | A | 8/1997 | Eppley et al. |
| RE37,249 | E | 6/2001 | Leibinger et al. |
| 6,254,639 | B1 | 7/2001 | Peckitt |
| 6,277,150 | B1 | 8/2001 | Crawley et al. |
| 6,302,884 | B1 | 10/2001 | Wellisz et al. |
| 6,551,608 | B2 | 4/2003 | Yao |
| 6,582,435 | B2 | 6/2003 | Wellisz et al. |
| 6,932,842 | B1 | 8/2005 | Litschko et al. |
| 7,747,305 | B2 | 6/2010 | Dean et al. |
| 8,298,292 | B2 | 10/2012 | Swards et al. |
| 8,781,557 | B2 | 7/2014 | Dean et al. |
| 9,208,558 | B2 | 12/2015 | Dean et al. |
| 9,275,191 | B2 | 3/2016 | Dean et al. |
| 9,292,920 | B2 | 3/2016 | Dean et al. |
| 9,330,206 | B2 | 5/2016 | Dean et al. |
| 2004/0138591 | A1 | 7/2004 | Iseki et al. |
| 2006/0094951 | A1 | 5/2006 | Dean et al. |
| 2006/0116682 | A1 | 6/2006 | Longo |
| 2006/0217813 | A1 | 9/2006 | Posnick et al. |
| 2007/0067041 | A1 | 3/2007 | Kotoske |
| 2012/0010711 | A1 | 1/2012 | Antonyshyn et al. |
| 2012/0203289 | A1 | 8/2012 | Beerens et al. |
| 2012/0259428 | A1 | 10/2012 | Brogan et al. |
| 2012/0265312 | A1 | 10/2012 | Burke et al. |
| 2012/0330427 | A1 | 12/2012 | Yaremchuk |
| 2012/0330435 | A1 | 12/2012 | Engqvist et al. |
| 2013/0206626 | A1 | 8/2013 | Schindel et al. |
| 2013/0289727 | A1 | 10/2013 | Rudnick et al. |

FOREIGN PATENT DOCUMENTS

| | | | |
|---|---|---|---|
| RU | 2074672 C1 | 3/1997 | |
| WO | WO-2017039762 A1 * | 3/2017 | ........... A61B 5/0006 |

OTHER PUBLICATIONS

HTR®-PMI CT-Scannning Protocol, Biomet HTR-PMI Brochure (date unknown).
Kelyniam Request for Quote form, undated.
KLS martin Group, Patient Contoured Mesh Order and Upload Form <http://pcm.klsmartinusa.com>, undated.
KLS martin Group, Patient Contoured Mesh Instructions <http://pcm.klsmartinusa.com/instructions.html>, undated.
OsteoMatch Patient Matched Implants, OsteoMed Neurosurgical, undated.
Osteosymbionics Clearshield Craniofacial Implant, undated.
Osteosymbionics, Custom Craniofacial Prosthesis CT Scanning Protocol, undated.
Osteosymbionics, ST Temporalis Soft Tissue Implant, undated.
Synthes CMF, CT Scanning Protocol Synthes Patient Specific Implants, Copyright 2007.
Synthes CMF, PSI-Patient Specific Implants, Derived from CT data excellent reconstructive results, Copyright 2004.
Stryker CMF Customized Implant PMMA, Surgical Protocol, Copyright 2013 Stryker.
Stryker CMF Customized Implant MEDPOR, Surgical Protocol, Copyright 2012 Stryker.
Sryker CMF Customized Implant PEEK, Surgical Protocol, Copyright 2013 Stryker.
Windhager, et al., "Limb Salvage in Periacetabular Sarcomas: Review of 21 Consecutive Cases", Reprinted from Clinical Orthopedics, Oct. 1996, vol. 331, pp. 265-276.
MEK Medizinelektronik GmbH, "three Dimensions. Nothing Less. Organ Models for Surgery Planning", Endoplan, Copyright 1988.
MEK Medizinelektronik GmbH, "Innovations made in Germany", Copyright Oct. 1988.
Howmedica, "Howmedica Computer Tomography Evaluation System (HCTE)", date unknown.
Voigt et al., "Three-dimensional reconstruction of a defect of the frontozygomatic area by custom made Proplast II implant", Eur J Plast Surg, 2000, pp. 391-394; 4 pages.

* cited by examiner

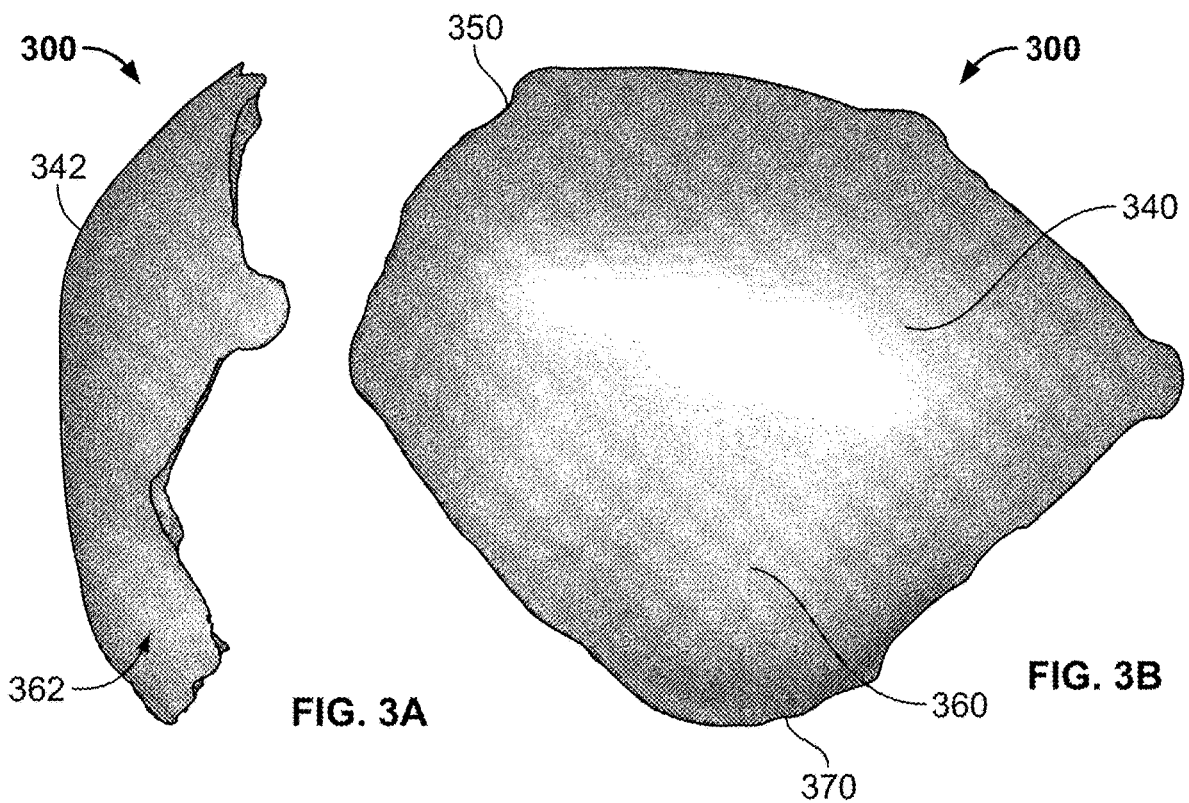
FIG. 3A
FIG. 3B
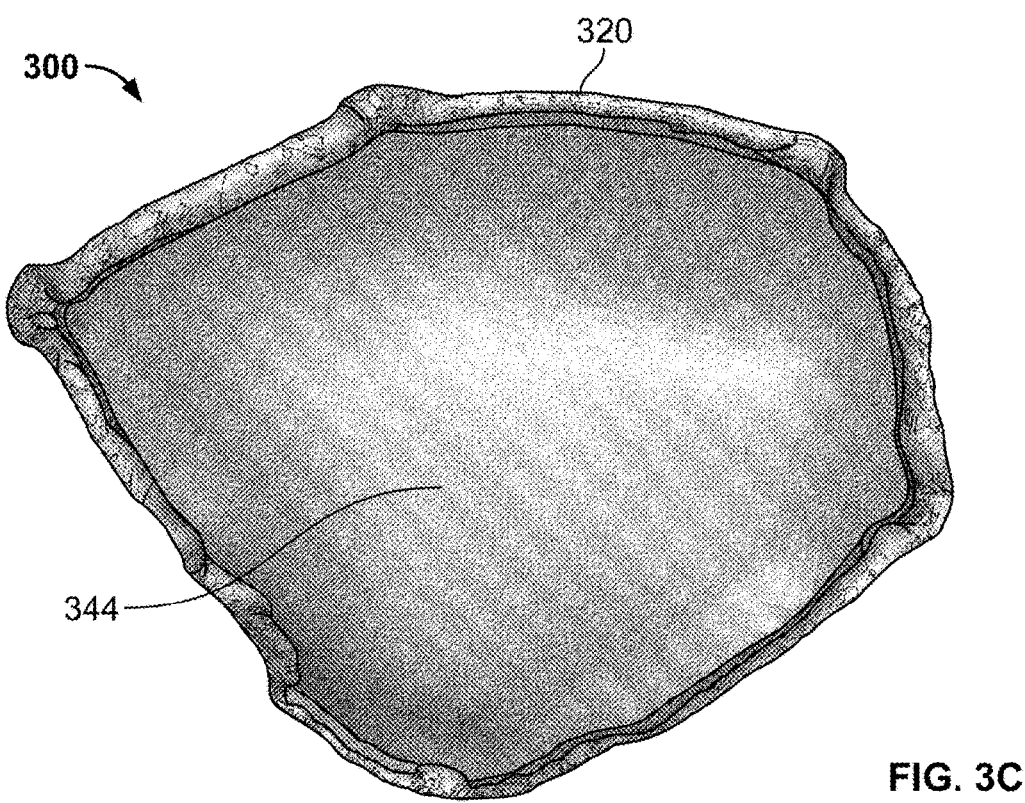
FIG. 3C

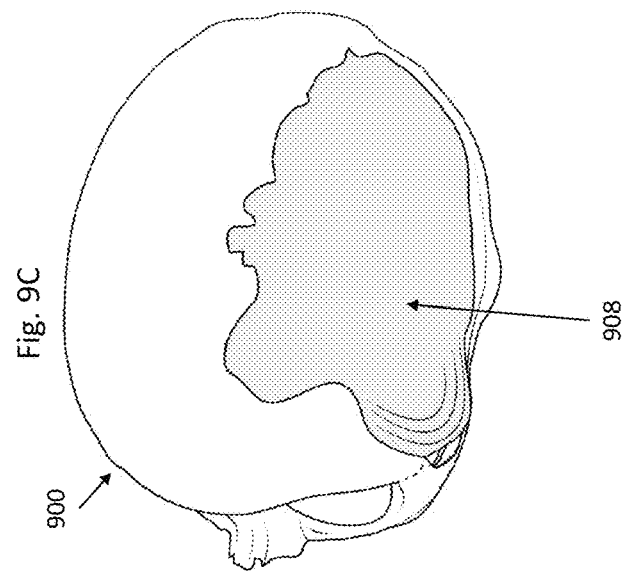
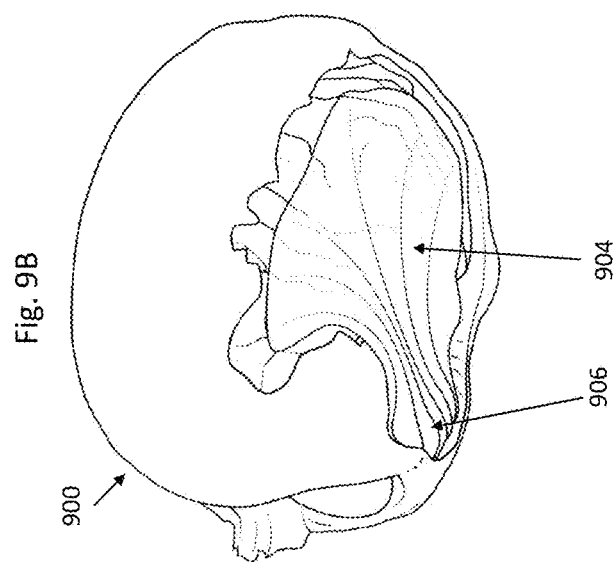
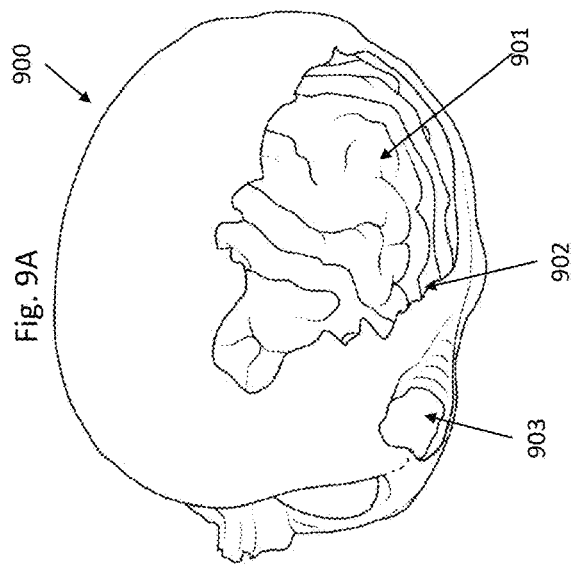

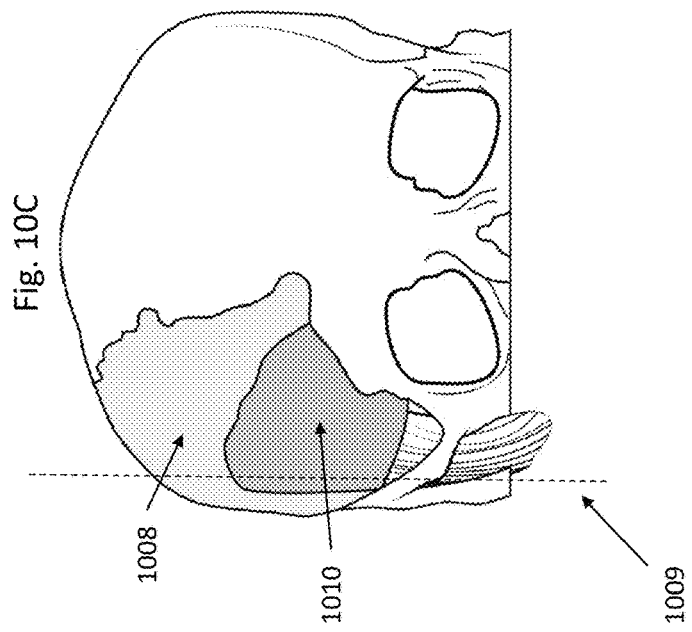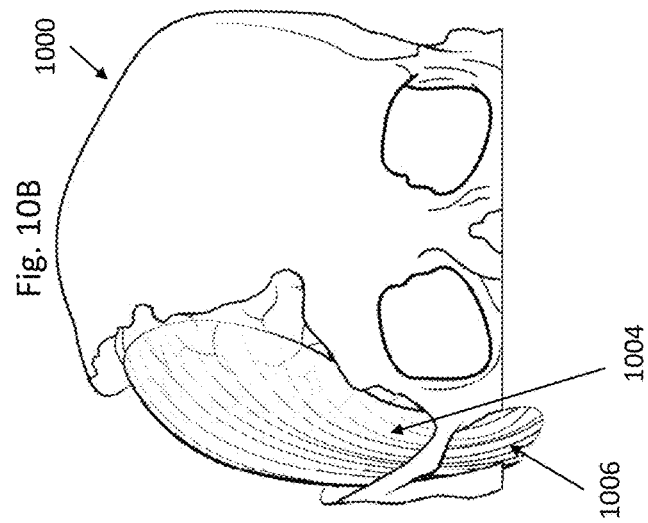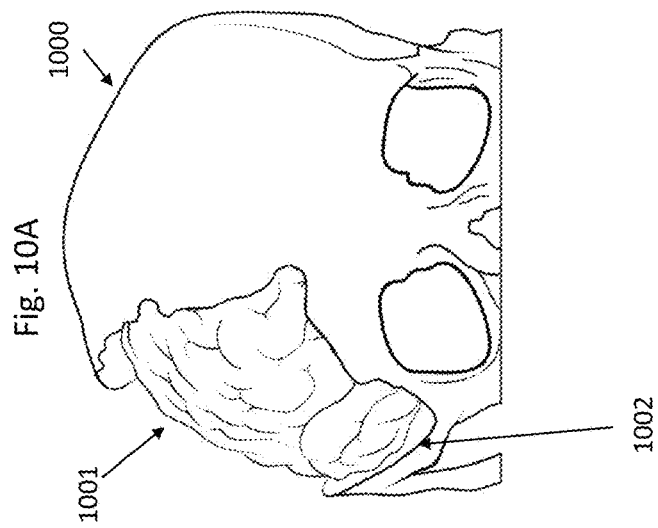

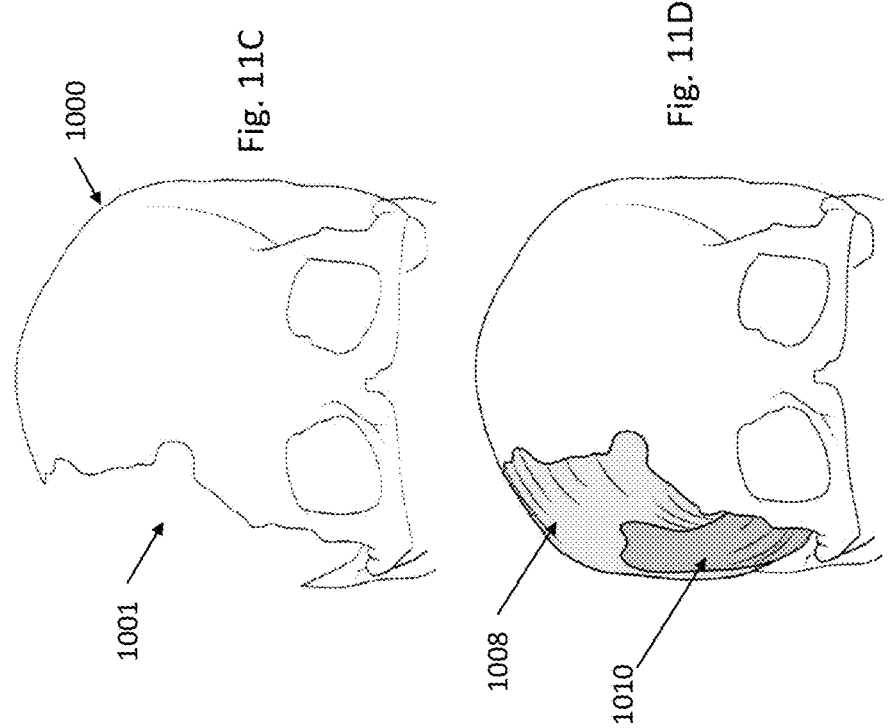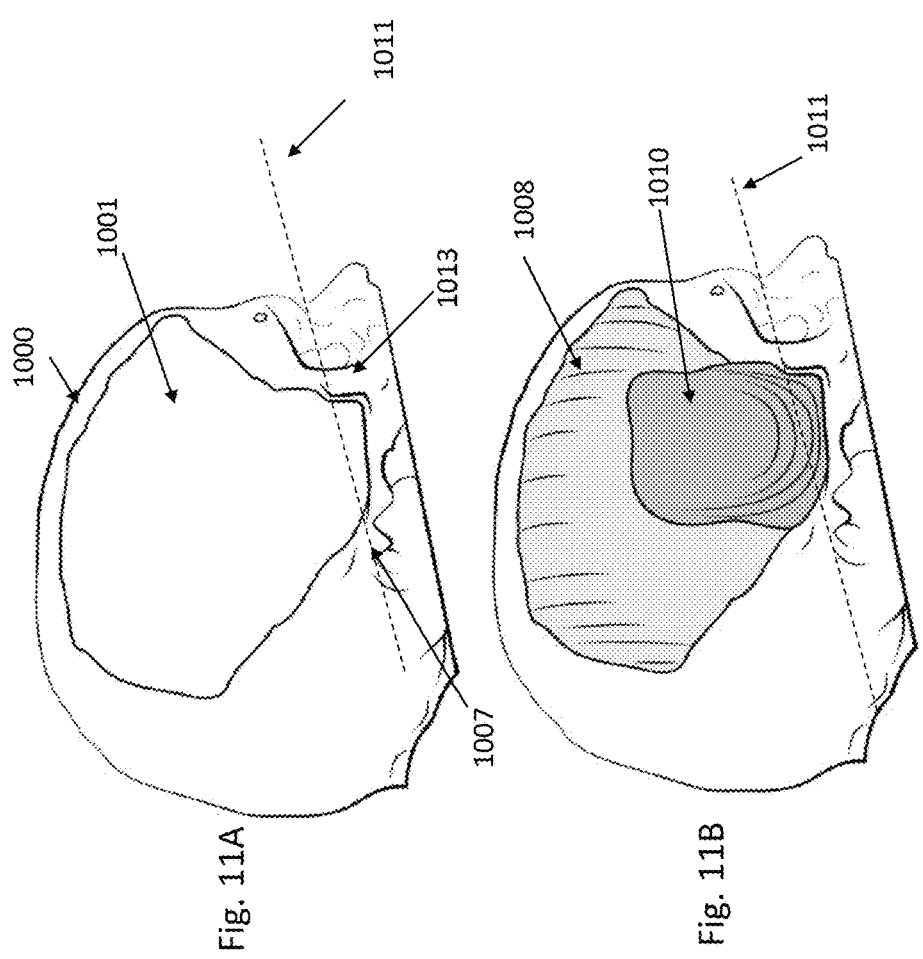

PATIENT-SPECIFIC CRANIOFACIAL IMPLANTS

CROSS-REFERENCE TO RELATED APPLICATIONS

The present application is a divisional of U.S. patent application Ser. No. 16/830,748, filed on Mar. 26, 2020, which is a divisional of U.S. patent application Ser. No. 16/377,455, filed on Apr. 8, 2019, which is a continuation in part of U.S. patent application Ser. No. 16/139,542, filed on Sep. 24, 2018, which is a continuation of U.S. patent application Ser. No. 14/958,161, filed on Dec. 3, 2015, which is a divisional of U.S. patent application Ser. No. 13/963,225, filed on Aug. 9, 2013. The disclosure of these applications is incorporated herein by reference.

FIELD

The present invention relates to patient-specific craniofacial implants and methods of designing such implants for filling both bone and soft tissue in the temporal region of a patient's head.

BACKGROUND

Certain congenital conditions and acquired deformities related to surgery, irradiation, and/or trauma may result in varying sized and shaped voids in bone and soft tissue. For example, severe impacts to the head could leave the frontal, parietal and/or temporal areas of the craniofacial skeleton in need of repair. Cranial bone voids are commonly filled throughout the anterior, middle, and posterior cranial vaults, for example, using autologous bone flaps, standard or customized alloplastic implants, titanium mesh, biologic absorbable materials, tissue engineered substrates and/or liquid methyl methacrylate in order to provide much needed cerebral protection. However, in times where secondary cranioplasty requires a bone substitute, temporal hollowing needs to be corrected and/or prevented.

While cranial bone voids present via congenital deformities or traumatic injuries may be filled using any one or more of the above means to achieve structural soundness, replacement of soft tissue structures that overlie the bone void being filled and underlie adjacent skin tissue generally has to be accounted for in order to achieve a preferable cosmetic result. Bone flaps, standard or customized alloplastic implants, titanium mesh, and liquid methyl methacrylate that are used to fill bone voids do not account for soft tissue atrophy in the temporal area of the skull. Thus, these bone void filling means do not provide an adequate aesthetic reconstruction of this area. The main problems are that the temporalis muscle and temporal fat pad change shape, thickness and location following temporary skull bone removal, and therefore, when the cranioplasty with custom skull implant is required, one is often challenged by having to mobilize the scarred down muscle and fat from its abnormal, inferior position and then try to re-attach it to the outside of currently-designed, patient-specific craniofacial implants.

In many cases where bone is filled in the temporal region, the soft tissue loss in this area generally results in concavity referred to as temporal hollowing, as originally described in detail by the surgeon-inventor in 2015 ["Quantitative analysis of dual-purpose, patient-specific craniofacial implants for correction of temporal deformity. *Operative Neurosurgery* 11(2):205-12" and "Craniofacial reconstruction with poly (methyl methacrylate) customized cranial implants. *Journal of Craniofacial Surgery* 26(1):64-70."] This deforming asymmetry reflects a deficiency in the bulk of the temporalis muscle or overlying temporal fat pad along the upper lateral face. Many patients who have undergone neurosurgical procedures that damage the integrity of the temporalis muscle during temporal or pterional craniotomy surgery in the temporal area are left with this concavity. Both aesthetic and reconstructive procedures that violate the temporal fat pad may also result in temporal hollowing. As such, the area of concern is a direct deformity related to a few etiologies such as temporalis muscle displacement or foreshortening from previous surgery, temporal fat pad atrophy, or soft tissue contraction from irradiation or aging. Thus, traditional implant methods require the surgeon to mobilize these scarred tissues off of the brain.

In patients with the common temporal hollowing, the top or cephalad part of the deformity is generally a concave depression due to the missing, above-mentioned etiologies. In addition, directly underneath and neighboring this concave depression is a convex bulge (directly cephalad to the zygomatic arch) that often originates from a displaced temporalis muscle. In some common instances, the temporalis muscle cannot be re-inserted since the bone flap is unable to be placed back into position, thereby leaving an absent fixation point adjacent the temporal crest. This not only accentuates the neighboring concave deformity above, it sometimes causes dynamic distortion during chewing since the temporalis muscle is involved with mastication.

Other reasons for the cephalad deficiency, or other head deformities, may entail temporal fat pad wasting, which is a defined layer of anatomical fat between the scalp and the skull which adds to the normal bulk of one's temporal region. It is often a sign of youthfulness. Many patients who have undergone neurosurgical and/or temporal procedures may lose the integrity of the temporalis muscle during temporal or pterional craniotomy surgery. Both aesthetic and reconstructive procedures that violate the temporal fat pad, such as coronal incisional approaches, for instance, may also result in temporal hollowing deformities, which can happen if a surgeon devascularizes the area with dissection or if the area has received irradiation or tissue resection for oncological treatment.

Numerous techniques have been described to augment the temporal area, including the placement of various standard or customized alloplastic implants, titanium mesh, free fat grafts, dermal grafts, tissue engineered substrates, the injection and onlay of various absorbable and permanent materials, loco-regional flaps, and, in some instances, free tissue transfer with microscopic technique. Temporal augmentation can restore the preoperative appearance of these patients; however, such augmentation is generally performed in a subsequent procedure after an initial procedure of filling a bone void in this area. Thus, these solutions are problematic because a revision surgery is generally required to correct the deformity, and the patient will likely exhibit aesthetic asymmetry prior to the revision surgery. There thus exists a need for a patient-specific cranial implant that provides both bony reconstruction and soft tissue reconstruction such that one or more revision surgeries will generally not be necessary. All previous implants follow the inferior, inward tapering of the normal temporal bone.

SUMMARY

As used herein, when referring to bones or other parts of the body, the term "superior" or "cephalad" means upper or top, and the term "inferior" or "caudal" means lower or bottom. The term "posterior" means towards the back of the body, and the term "anterior" means towards the front part of the body or the face. The term "medial" means toward the midline or center of the body, and the term "lateral" means away from the midline or outside of the body.

The patient-specific, dual-purpose temporal implants of the present invention are designed to fill a void in the skull while also simultaneously augmenting the pterional/temporal area. Preferably, alloplastic material is used in the construction of such patient-specific temporal implants. The mechanical properties of the alloplastic material used to construct these implants will allow them to cover the void and to recreate the soft tissue bulk that is preferably present in the temporal area prior to any injury and/or atrophy occurring in a patient. The patient-specific implants of the present invention are designed to fill a cranial void while also restoring aesthetic symmetry by augmenting the temporal area of the skull to counter temporal hollowing. Therefore, the patient-specific cranial implants of the present invention may be used to replace a bony void left by a craniotomy either as a preemptive or prophylactic solution to addressing aesthetic asymmetry that may occur due to atrophy of temporal muscle or overlying fat pad of the bony void.

A first aspect of the present invention is a method of designing a patient-specific craniofacial implant for filling a void in a patient's skull and for simultaneously replacing soft tissue comprises first creating a three dimensional model of the skull having the void, then creating a preliminary implant model configured to replace the void in the skull, and then creating an updated implant model by augmenting an outer contour of the preliminary implant model to account for soft tissue loss or displacement in a temporal area such as the pterional region of the skull overlying at least a portion of the bony void. A second aspect is to create a "temporal trim" or virtual window to prevent muscle impingement when using the implant in an overlay position (above the scarred down tissue) within the temporal fossa.

In one embodiment of this first aspect, tomographic images of the skull of the patient are taken in order to create the three-dimensional model of the skull including the void. The preliminary model is created by mirroring contralateral bone of the void about a sagittal plane of the patient. If the defect is bilateral, normal variations of soft tissue to hard tissue variance may be assessed by industry standards and utilized for unilateral or bilateral temporal implant fabrication. Such assessments may be made as gender-specific for males and females since they are known to have different gender-specific anthropometrics.

In another embodiment of this first aspect, creating a three dimensional of the skull having the void may include taking two-dimensional or three-dimensional photographs from various views for confirmation of aesthetic deformity size and/or shape of the void. It may also include creating a "single-stage custom implant" design. This type of novel design would allow the surgeon to virtually plan an oncological resection of a skull tumor (or brain tumor invading a skull) and add several centimeters of extra implant material around the edges. This type of advance would allow one to resect a skull tumor and then immediately use a dual-purpose, patient-specific craniofacial implant to restore the oncological defect to proper symmetry in hopes of avoiding a post-operative temporal deformity.

In another embodiment of this first aspect, augmenting the outer contour of the preliminary implant model comprises providing a first cross-sectional view of the preliminary implant model in a coronal plane, providing on the first cross-sectional view a vertical line tangent to a most lateral portion of a zygomatic arch of the skull of the patient, and providing on the first cross-sectional view a contour line from a temporal crest of the skull until the contour line intersects the vertical line tangent to the most lateral portion of the zygomatic arch in the first cross-sectional view, the contour line representing a first portion of the augmented outer contour of the preliminary implant model. Following this embodiment, the implant model may be trimmed accordingly using a vector spanning between the zygomatic process of the temporal bone and the zygomatic-frontal suture of the lateral orbital rim to allow placement and positioning over the scarred down temporalis muscle.

In yet another embodiment of this first aspect, augmenting the outer contour of the preliminary implant model further comprises providing a second cross-sectional view of the preliminary implant model in a coronal plane, providing on the second cross-sectional view a vertical line tangent to a most lateral portion of a zygomatic arch of the skull of the patient, and providing on the second cross-sectional view a contour line from a temporal crest of the skull until the contour line intersects the vertical line tangent to the most lateral portion of the zygomatic arch in the second cross-sectional view, the contour line representing a second portion of the augmented outer contour of the preliminary implant model. The coronal plane of the first cross-sectional view is more posterior than the coronal plane of the second cross-sectional view.

In still yet another embodiment of this first aspect, augmenting the outer contour of the preliminary implant occurs in a plurality of cross-sectional views in the coronal plane.

In still yet another embodiment of this first aspect, augmenting the outer contour of the preliminary implant occurs in a plurality of cross-sectional views in an axial plane.

In still yet another embodiment of this first aspect, augmenting the outer contour of the preliminary implant occurs in a plurality of cross-sectional views in a sagittal plane.

In still yet another embodiment of this first aspect, the patient-specific craniofacial implant is manufactured from alloplastic and/or absorbable biologic materials selected from one member of a group consisting of polymethylmethacrylate (PMMA), polyetheretherketone (PEEK), porous high-density polyethylene (MedPor), or any other FDA-approved biomaterial. Other biologic materials or tissue-engineered substrates may also be used in both allograft and xenograft origin using the patient-specific craniofacial implant design processes described herein.

A second aspect of the present invention is a craniofacial implant comprising a base portion having an outer surface curved in a medial to lateral direction, a superior to inferior direction, and a posterior to anterior direction, and a curved augment portion protruding outwardly from the outer surface of the base portion in the medial to lateral direction to restore proper appearance anywhere along the temporal skeleton when both a hard tissue deformity and soft tissue deformity co-exist. The craniofacial implant of the present invention could also be designed for soft-tissue only defects, providing the surgeon a new method to camouflage asymmetries—both from congenital and acquired etiologies.

In one embodiment of this second aspect, the curved augment portion of the craniofacial implant has an outer surface curved in the medial to lateral direction, the superior to inferior direction, and the posterior to anterior direction.

In another embodiment of this second aspect, the outer surface of the base portion and the augment portion has a first radius of curvature in the medial to lateral direction, and wherein the first radius of curvature of the base portion is larger than the first radius of curvature of the augment portion.

In yet another embodiment of this second aspect, the outer surface of the base portion and the augment portion has a second radius of curvature in the superior to inferior direction, and wherein the second radius of curvature of the base portion is larger than the second radius of curvature of the augment portion.

In yet another embodiment of this second aspect, the outer surface of the base portion and the augment portion has a third radius of curvature in the posterior to anterior direction, and wherein the third radius of curvature of the base portion is larger than the third radius of curvature of the augment portion.

In yet another embodiment of this second aspect, the outer surfaces of the base portion and the augment portion are convex.

In still yet another embodiment of this second aspect, the base portion and the augment portion each have concave inner surfaces.

In still yet another embodiment of this second aspect, the base portion has a lateral side that forms a perimeter of the craniofacial implant.

In still yet another embodiment of this second aspect, the augment portion has a lateral side that forms a portion of a perimeter of the base portion.

In yet another exemplary embodiment of the second aspect, the temporal portion has an anterior extension that forms an onlay prosthesis (as opposed to a full-thickness defect replacement prosthesis) used for temporal deformity prevention and/or correction for which may even extend to the lateral orbital rim and cover areas of intact skull.

BRIEF DESCRIPTION OF THE DRAWINGS

A more complete appreciation of the subject matter of the present invention and the various advantages thereof can be realized by reference to the following detailed description in which reference is made to the accompanying drawings in which:

FIG. 3A is a frontal view of one embodiment of a patient-specific cranial implant of the present invention designed to fill a bone void in a skull of a patient and to simultaneously correct co-existing temporal muscle/fat deficiencies contributing to deformity.

FIG. 3B is a lateral view of an outer surface of the patient-specific cranial implant of FIG. A.

FIG. 3C is a lateral view of an inner surface of the patient-specific cranial implant of FIG. 3A.

FIG. 9A is an exemplary view of a pre-existing skull and facial defect in need of a customized cranial implant.

FIG. 9B is an exemplary diagram of a custom cranial implant and method of implantation.

FIG. 9C is an exemplary diagram of a custom cranial implant as implanted.

FIG. 10A is an exemplary view of a pre-existing skull and facial defect in need of a customized cranial implant.

FIG. 10B is an exemplary diagram of a custom cranial implant and method of implantation.

FIG. 10C is an exemplary diagram of a custom cranial implant as implanted.

FIG. 11A is an exemplary view of a pre-existing skull and facial defect in need of a customized cranial implant.

FIG. 11B is an exemplary diagram of a custom cranial implant as implanted.

FIG. 11C is an exemplary view of a pre-existing skull and facial defect in need of a customized cranial implant.

FIG. 11D is an exemplary diagram of a custom cranial implant as implanted.

DETAILED DESCRIPTION

Figure 1A:
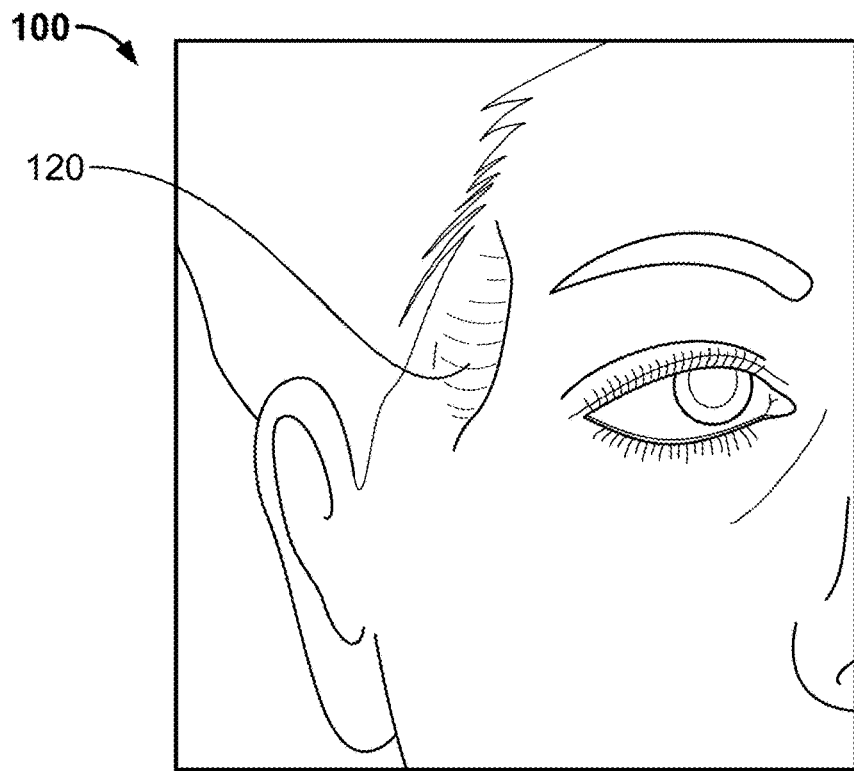
FIG. 1A is a perspective view of a patient's face exhibiting temporal hollowing deformity in the pterional or temporal region of the skull or face.

FIG. 1A is a perspective view of a patient's face 100 exhibiting temporal hollowing 120 in the pterional or temporal region of the skull and face of the patient. The size, shape and location of such temporal hollowing deformity of a patient may differ based on patient's anatomy as well as the type of injury and/or the amount of tissue atrophy incurred by the patient in this region.

Figure 1B:
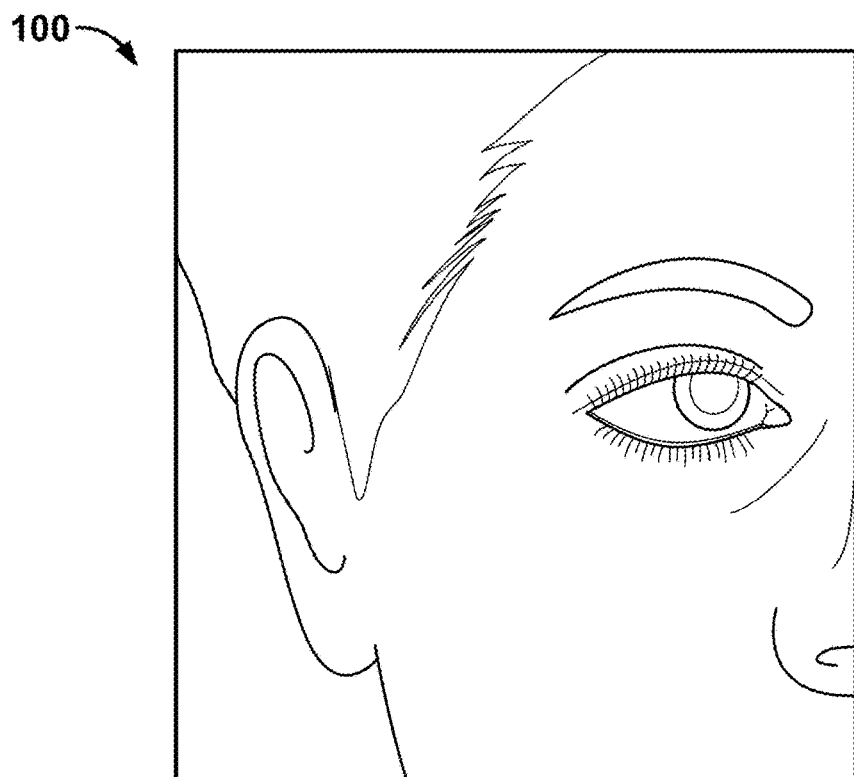
FIG. 1B is a perspective view of the patient's face of FIG. 1A with a repaired pterional or temporal region such that the temporal hollowing has been corrected.

FIG. 1B is a perspective view of the patient's face with a repaired pterional or temporal region such that the temporal hollowing deformity has been corrected and is no longer present. After an initial surgery to correct a bony void is performed, a subsequent procedure using a pterional graft, liquid PMMA, dermal filler, absorbable material or tissue engineered substrate, for example, may be performed in order to repair the soft tissue defect. The subsequent procedure may be conducted via injection of PMMA percutaneously into this region or by placing a pterional flap through a small incision made in the skin. However, a patient will likely exhibit aesthetic asymmetry between the time of the initial surgery and the subsequent revision surgery to correct the temporal hollowing deformity shown in FIG. 1A. Soft tissue reconstruction will change with the respect to time and is suboptimal versus a solid, computer-designed implant with stable and durable design/shape. The patient-specific cranial implants and methods of designing such implants of the present invention together provide simultaneous customized hard tissue (i.e. bony) reconstruction and soft tissue (i.e. fat/muscle) reconstruction in a single procedure approach such that temporal hollowing deformity is avoided and revision procedures will not be required.

Figure 2:
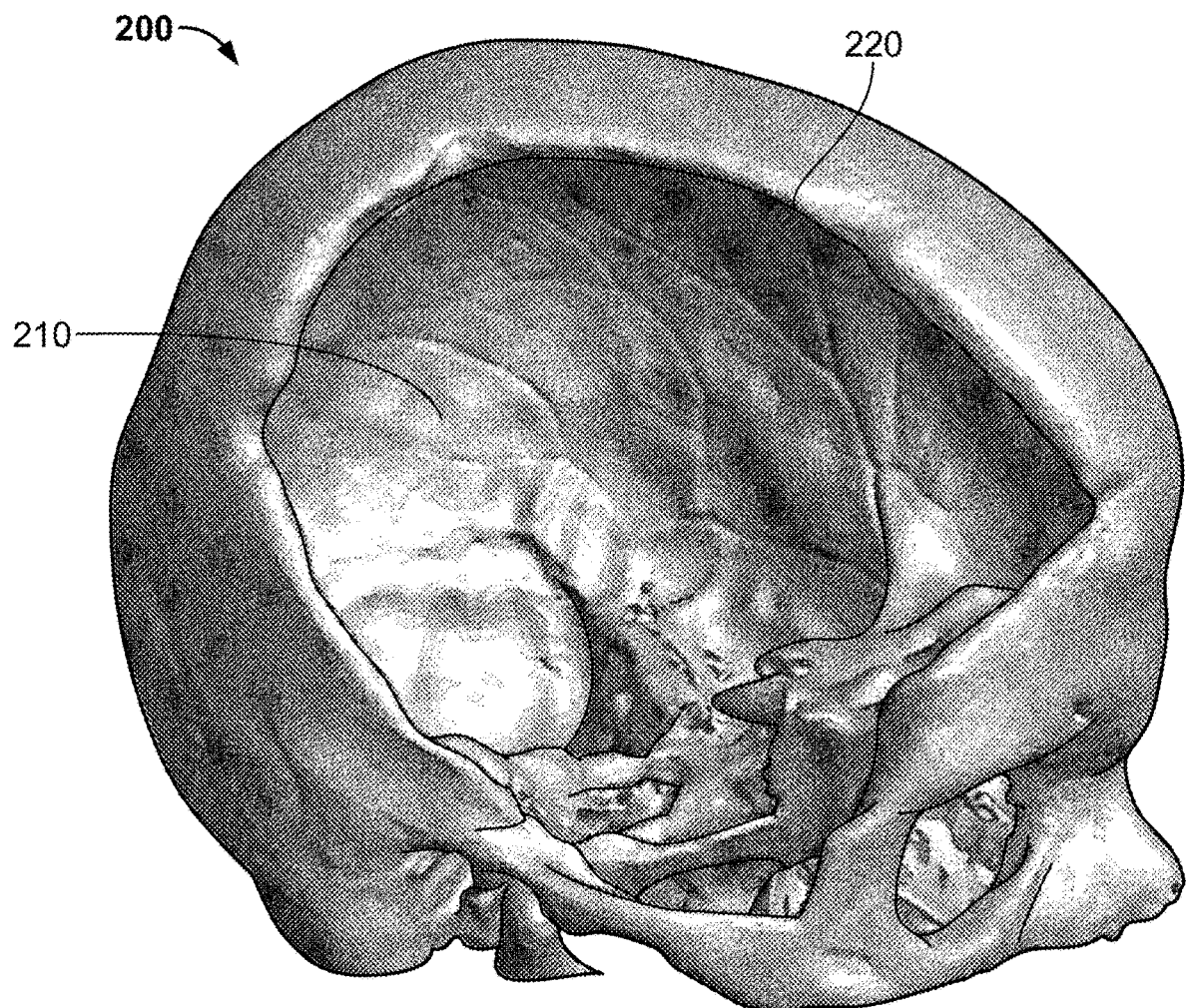
FIG. 2 is a perspective view of a patient's skull or lateral face exhibiting a large bone void predominately positioned in the temporal lobe thereof.

FIG. 2 is a perspective view of a patient's skull 200 exhibiting a large irregularly shaped bone void 210 predominately positioned in the temporal lobe thereof. FIGS. 3A-3C show one embodiment of a patient-specific cranial implant 300 of the present invention designed to fill a bone void, such as shown in FIG. 2, for example. Patient-specific cranial implant 300 includes a perimeter 320 configured to contact a perimeter 220 of bone void 210 when patient-specific cranial implant 300 is coupled to bone void 210 in a preoperatively planned position. Upon coupling of patient-specific cranial implant 300 to bone void 210, plates, fasteners and/or adhesive glue, for example, may be used around perimeters 220, 320 of bone void 210 and implant 300, respectively, in order to fix the position of implant 300 with respect to bone void 210. A description of such plates and fasteners used to couple a patient-specific implant to a perimeter of a bone void is shown and described in the surgical protocol titled "Stryker CMF Customized Implant PEEK," the disclosure of which is incorporated by reference herein in its entirety. Of note, the implants from this surgical protocol (as shown) are designed to have contact within the skull defect and complete 360-degree fixation once the temporalis muscle is removed from its scarred position on top of the brain. They are not designed to flare outwards and/or to have a dual-purpose design other than to simply replace the missing temporal bone.

Implant 300 includes a base portion 340 and an augment portion 360. Base portion 340 includes a convex outer surface 342 and a concave inner surface 344. Outer and inner surfaces 342, 344 of base portion 340 are preferably curved in a superior to inferior direction, a posterior to anterior direction, and a medial to lateral direction. Augment portion 360 protrudes outwardly from base portion 340 in the medial to lateral direction. Augment portion 360 includes a convex outer surface 362 that is also preferably curved in the superior to inferior direction, the posterior to anterior direction, and the medial to lateral direction.

Base portion 340 and augment portion 360 each have a first radius of curvature in the superior to inferior direction, a second radius of curvature in the posterior to anterior direction and a third radius of curvature in the medial to lateral direction. The first, second and third radii of curvature of the base portion 340 are all larger than the first, second and third radii of curvature of the augment portion 360, respectively. Therefore, base portion 340 is flatter and not as steeply shaped as augment portion 360. The radii of curvature are generally not constant along any one direction for each of the base portion 340 and augment portion 360.

Augment portion 360 has a lateral side 370 that preferably forms a portion of a perimeter 350 of base portion 340. The location of augment portion 360 with respect to base portion 360 is such that lateral side 370 of augment portion 360 preferably forms a portion of perimeter 320 of implant 300 along with perimeter 350 of base portion 340.

When cranial implant 300 is implanted, the most lateral portion of outer surface 362 of augment portion 360 is preferably located on a line tangent to the most lateral portion of the zygomatic arch, the line being substantially parallel to the sagittal plane of the patient. Augment portion 360 also extends as far posteriorly as it does superiorly so that an area of augment portion is roughly square. The augmented portion terminates at a limit known and described as a temporal trim line—which is a consistent vector spanning the zygomatic process of the temporal bone and the zygomatic-frontal suture line of the lateral orbital bone.

A method of designing a patient-specific craniofacial implant, such as cranial implant 300, for filling a void in a skull or face of a patient and for replacing soft tissue is shown in FIGS. 4A-6B. A tomographic scan such as a computed tomography ("CT") scan of a patient with a lateral cranial or facial defect that fully or partially extends into the pterional or temporal region of the skull and face is first taken. Off the shelf CT segmentation software is then used to create a three dimensional ("3D") model of the patient's cranium including the lateral cranial or facial defect. A patient-specific craniofacial implant is then designed using computer aided design ("CAD") software. The patient-specific 3D implant will fill the bony void left by a craniotomy, for example, and also augment the visible temporal portions of the patient's head. When and if needed or desired, an additional extension of thin material can extend from the anterior boundaries of the implant as an overlay (above intact skull or facial bone) and abut the lateral orbital rim along the temporal fossa area.

In some further exemplary embodiments, an augmentation of the outer contour of the preliminary implant model to account for facial soft tissue loss overlying at least a portion of the bony void may further include the creating of a purposeful gap (i.e. temporal trim). The gap may be formed as a consistent and valuable "temporal trim" to avoid painful compression of the temporalis muscle left undisturbed underneath the implant, as opposed to suspending it on the outside of the implant which is done in normal fashion. Further, an extra portion of material may be created or used as an added extension that abuts the lateral orbital rim to the extent of the zygoma's later projection, which is outside the confines of the actual full-thickness skull defect.

Figure 4A:
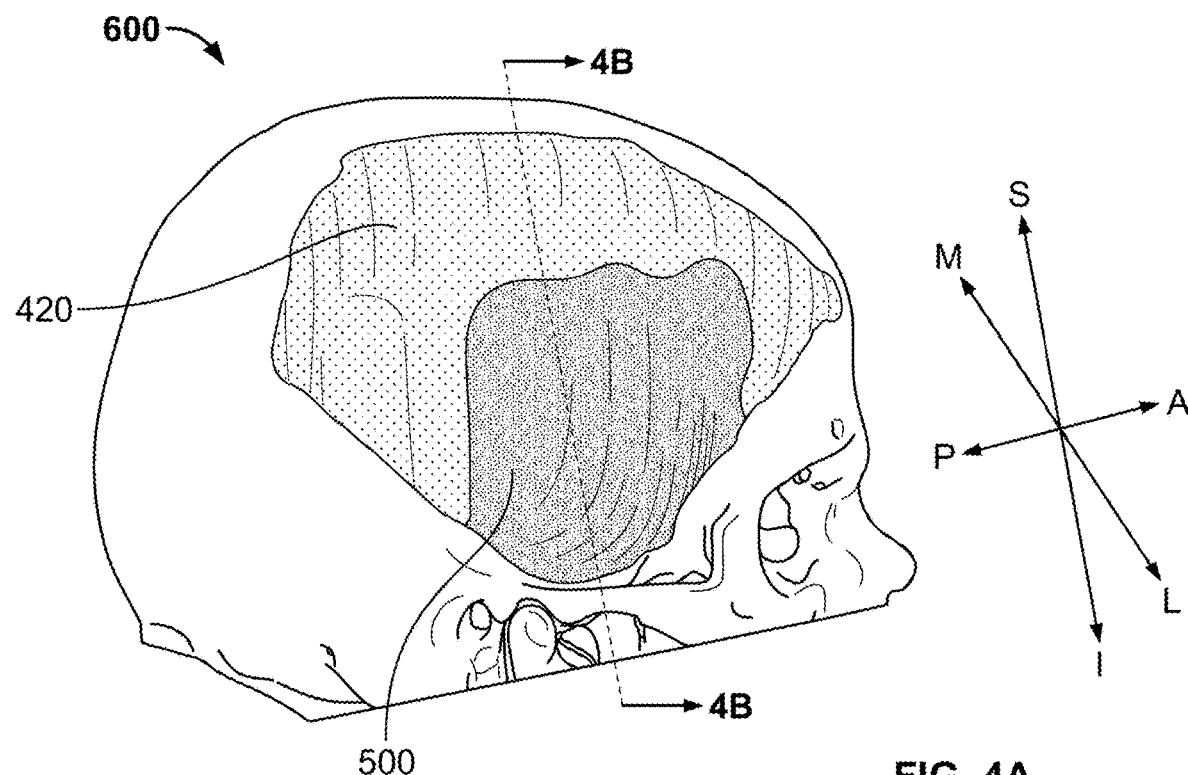
FIG. 4A is a 3D reconstruction of a patient-specific cranial implant of the present invention having filled a void in the skull or lateral face of a patient, the patient-specific cranial implant having an augmented portion projecting outwardly from a base portion.
Figure 4B:
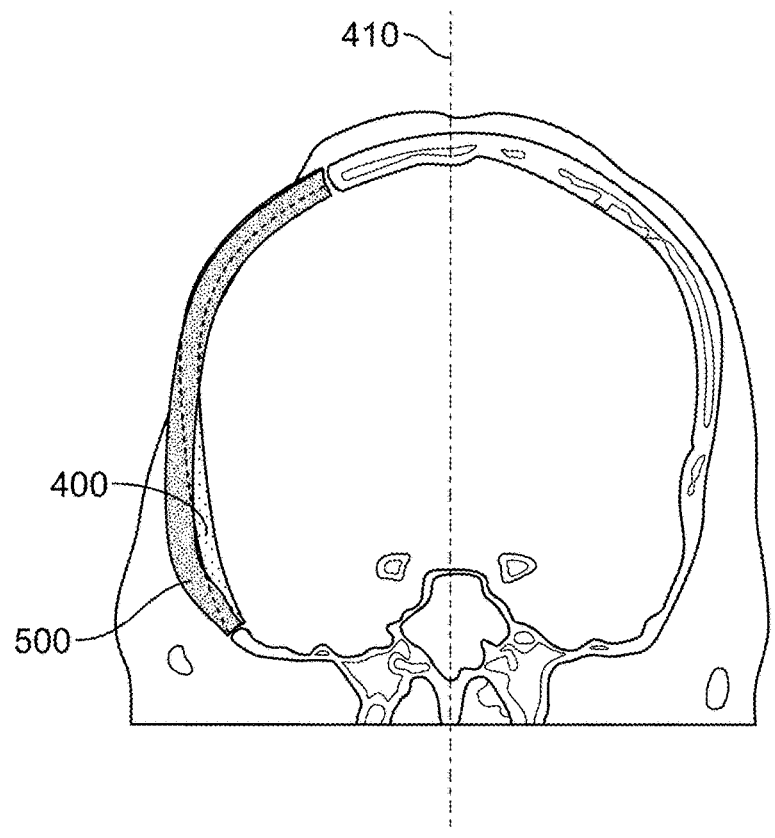
FIG. 4B is a coronal cross-section of the 3D reconstruction of FIG. 4A taken along the section line shown in FIG. 4A, the cross-section showing the relationship between the base portion and the augmented portion of the patient-specific cranial implant.

Using the CAD software, a preliminary implant model 400 is designed by mirroring contralateral bone of the lateral cranial or facial defect. Generally, the contralateral bone is mirrored off of the central sagittal plane 410 as shown in FIG. 4B of a patient's skull or face in order to define the size, shape and location of preliminary implant model 400 with respect to the cranial or facial defect. Models of deformed or missing segments of internal structures, such as a lateral cranial and facial defect, may also be constructed from coordinate data specifying the deformed or missing segment that is derived from representations of a normal mirror image segment of the structure. For example, coordinate data defining a mirror image segment of a structure is useful in the construction of an implantable prosthetic inlay that is to replace a missing segment of a generally symmetrical internal anatomic structure as shown and described in U.S. Pat. No. 4,436,684 to White entitled, "Method of Forming Implantable Prosthesis for Reconstructive Surgery," the disclosure of which is hereby incorporated by reference in its entirety. In instances where bilateral deformities exist, the dual-purpose implants of the present invention may be at least partly designed using standard gender-specific dimensions.

While preliminary implant model 400 may be designed using any one or more of the above described methods, it represents a traditional customized implant that does not account for soft tissue in the pterional/temporal region. It can also have a single-use design to replace any and all missing cranial bone, as opposed to a dual-purpose design for which has thin onlay extensions nearby to adjust for any missing soft tissue. It also doesn't account for leaving the temporal muscle down against the brain and requires the surgeon to mobilize the muscle off of the brain at time of placement. In a method of the present invention, preliminary implant model 400 is used as a guide during subsequent design steps. The outer contour 420 of preliminary implant model 400 is augmented in order to account for the soft tissue loss. This novel shape and design allows for the surgeon to position the implant above the scarred down muscle by way of a "temporal trim window" design.

Preliminary implant model 400 is designed to have a perimeter that contacts the entire perimeter of the bone void. Augment portion 500 is designed to augment the pterion in order to counter the effects of temporal hollowing deformity. Careful attention is made not to include excess material inferiorly which may contribute to mandibular interference known as trismus. This excess material is removed at the temporal trim line on a vector consistent between two reliable anatomical landmarks, the zygomatic process of the temporal bone and the zygomatic-frontal suture line along the lateral orbital rim. The CT coronal cross section of FIG. 4B shows the difference between preliminary implant model 400 and an updated implant model including augment portion 500. In some design processes, augment portion 500 may only project outwardly from preliminary implant model 400 such that it does not span the entire length of a bone void, and therefore does not contact the entire perimeter of the bone void as does the preliminary implant model. By not contacting the inferior bone edge, the design allows for an augmented design and does not mirror the temporal bone as it tapers inward. As can be seen in FIG. 4B, for example, augment portion 500 is not symmetric to contralateral bone as is preliminary implant model 400. Together, preliminary implant model 400 and augment portion 500 form an updated implant model 600 as shown in FIG. 4A. Preliminary implant model 400 has a first volume and augment portion 500 has an additional volume. With the addition of the volume of augment portion 500 to the first volume of preliminary implant model 400, updated implant model 600 therefore has a second volume greater than the first volume. This figure also includes a directional legend with arrows in three dimensions. S, I, M, L, P and A on this legend, and any other legend in the drawings, stand for superior, inferior, medial, lateral, posterior and anterior, respectively. Most of the bulk reproduction of the soft tissue in the pterion or temporal region, which is represented by augment portion 500, occurs at the anterior, lateral, inferior portion of the temporal skull and face.

Figure 5A:
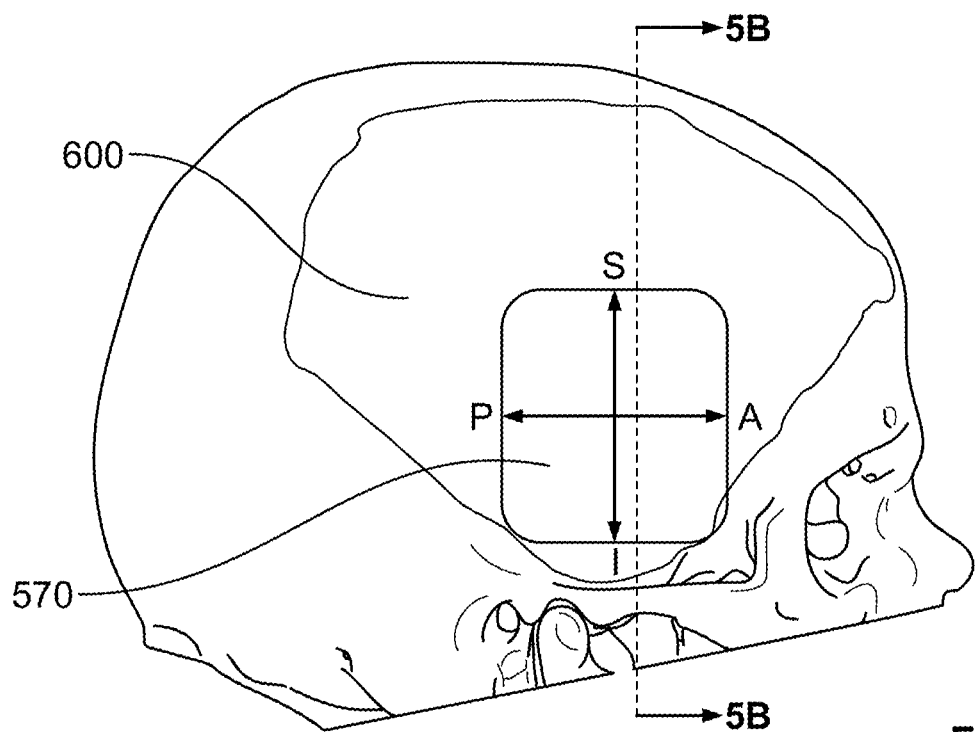
FIG. 5A is a 3D reconstruction of the patient-specific cranial implant of FIG. 4A wherein the augmented portion thereof is shown having an area approximately the area of the box with arrows overlying the implant.
Figure 5B:
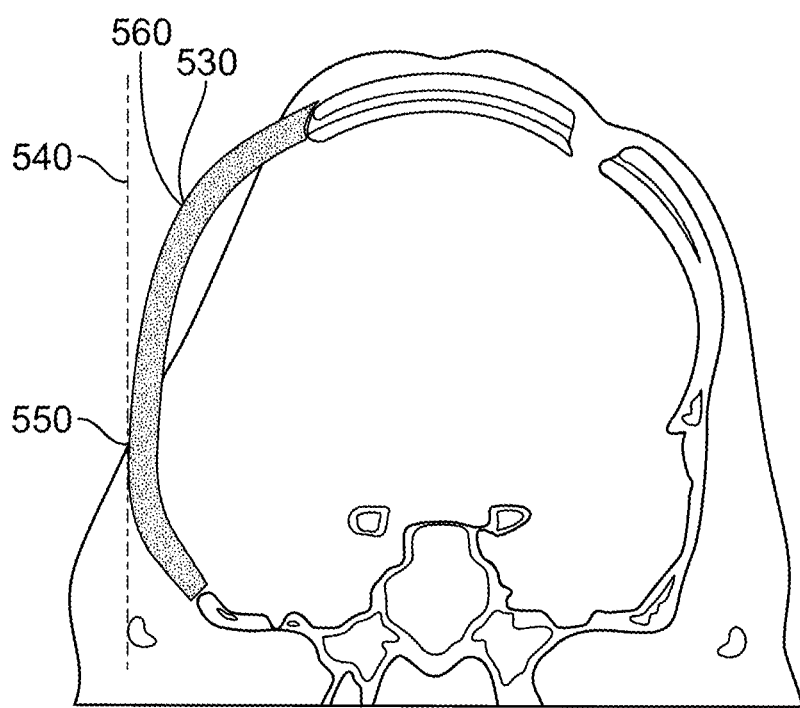
FIG. 5B is a coronal cross-section of the 3D reconstruction of FIG. 5A taken along line 5B thereof showing the location of the most lateral portion of the augmented portion of the patient-specific cranial implant.

In determining the location of the most lateral portion of the outer surface of augment portion 500, the preliminary implant model 400 is extended laterally away from sagittal plane 410, for example, until the outer surface of augment portion 500 meets the most lateral portion of the zygomatic arch 550 of the patient as shown in FIG. 5B. The most lateral portion of the zygomatic arch is depicted by vertical line 540 in the coronal cross section shown in FIG. 5B. In the coronal plane, the temporal region of the preliminary implant model is augmented by drawing a substantially straight or slightly curved line 560 from the temporal crest 530 until line 560 intersects vertical line 540 adjacent the most lateral portion of the zygomatic arch 550. Temporal crest 530 is located at the point where there is a change in tangency of the pterional skull as pertinent in the present scenario. Of note, various other areas of the temporal (i.e. pterional) skeleton could be assessed for dual-purpose reconstruction. This process is preferably repeated in several different two dimensional ("2D") coronal cross-sections. The updated implant models created in the 2D cross-sections are then combined using the CT segmentation software in order to create the 3D updated implant model shown in FIGS. 6A-6B, for example.

Figure 6A:
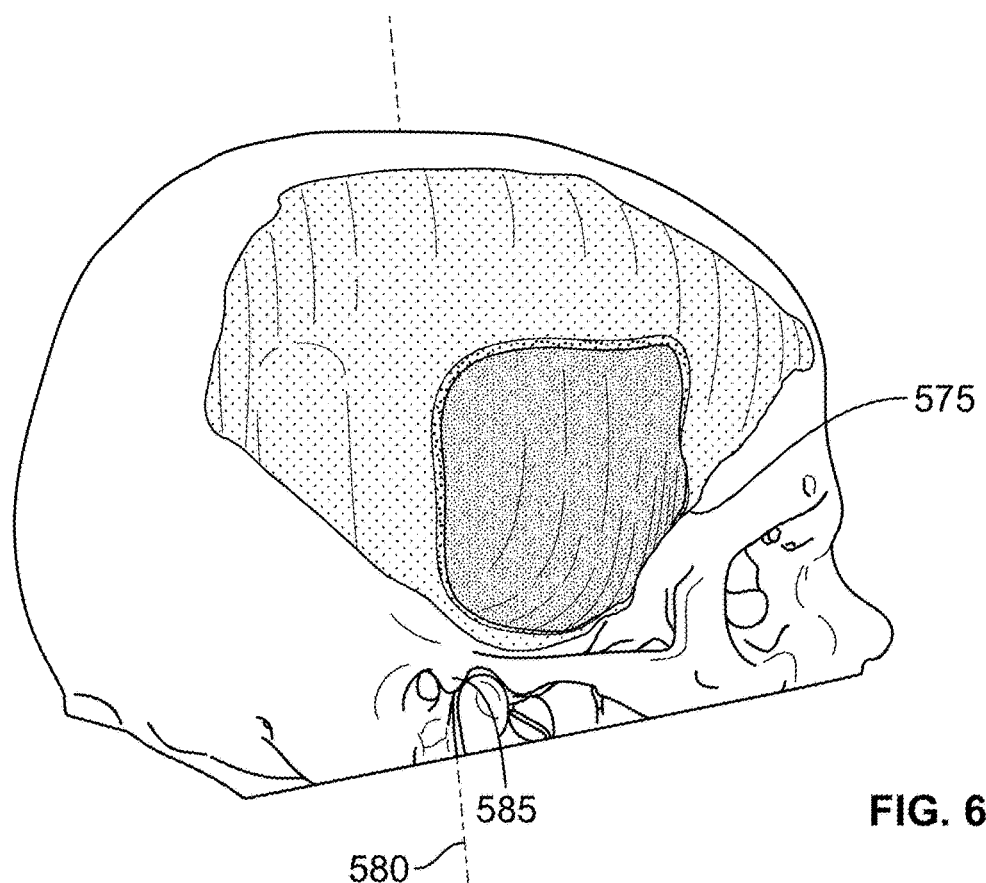
FIG. 6A is a lateral view of the 3D reconstruction of the patient-specific cranial implant.
Figure 6B:
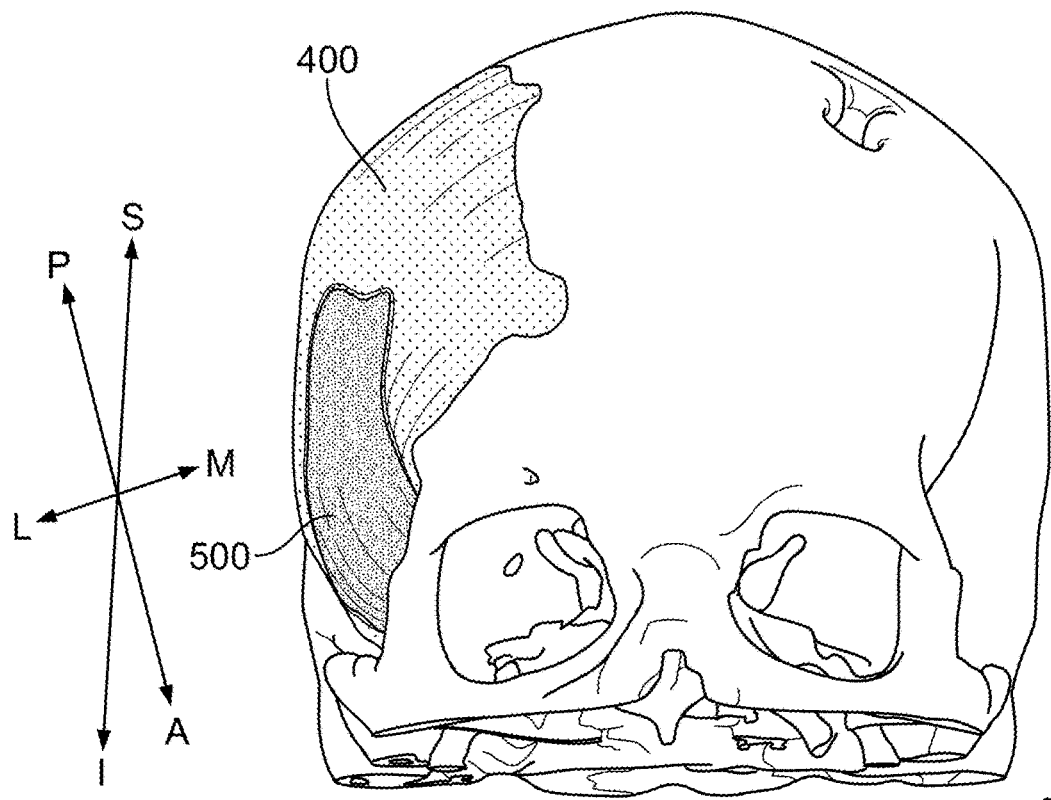
FIG. 6B is a frontal view of the 3D reconstruction of the patient-specific cranial implant shown in FIG. 6A.

As shown in FIGS. 6A-6B, augment portion 500 extends posteriorly from the lateral orbital rim 575 to a vertical line 580 perpendicular to the sagittal plane drawn through the external acoustic meatus 585. Augment portion 500 should extend as far posteriorly as it does superiorly so that the augmented area is roughly square as shown in FIG. 5A. The augmented area is roughly outlined by box 570 overlying updated implant model 600 in FIG. 5A.

Figure 7A:
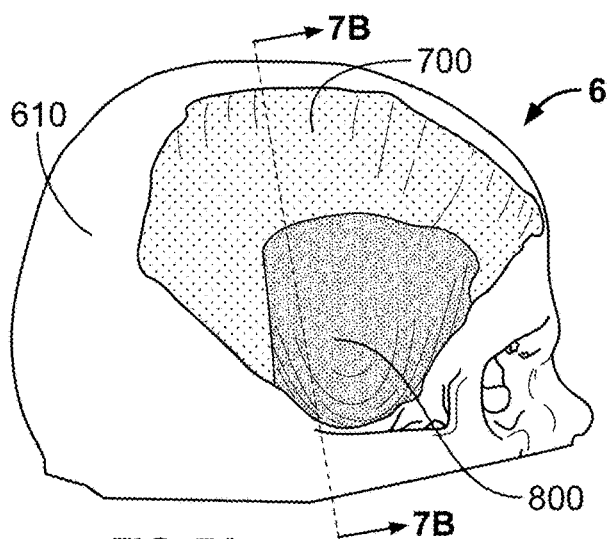
FIG. 7A is a lateral view of a 3D reconstruction of another embodiment of a patient-specific cranial implant having a base portion and at least one augmented portion.
Figure 7B:
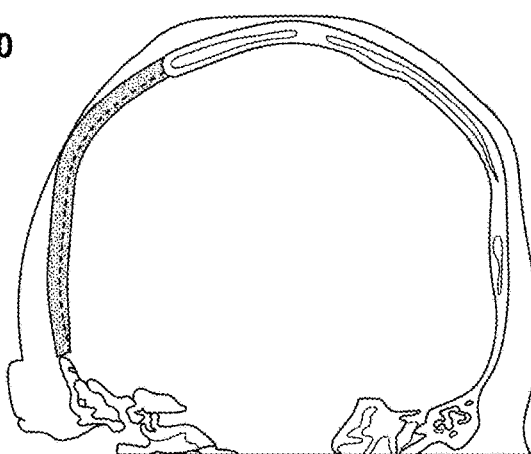
FIG. 7B is a coronal cross-section of the 3D reconstruction of FIG. 7A taken along line 7B thereof, the cross-section showing the configuration of the base portion and the augmented portion at a posterior location of the pterional or temporal region of the skull and face.
Figure 7C:
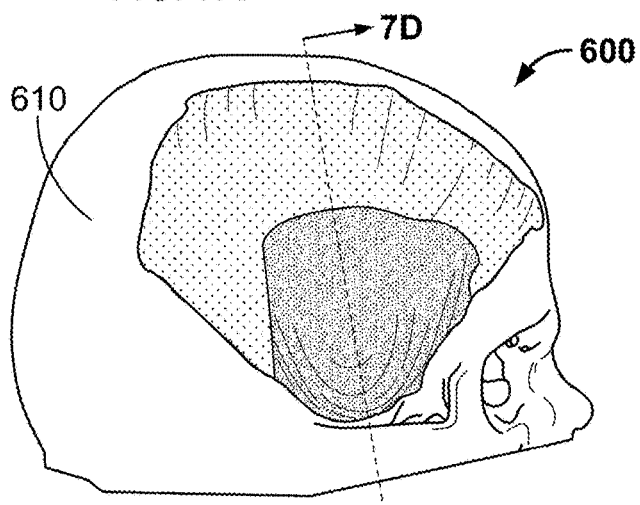
FIG. 7C is another lateral view of a 3D reconstruction of the patient-specific cranial implant of FIG. 7A.
Figure 7D:
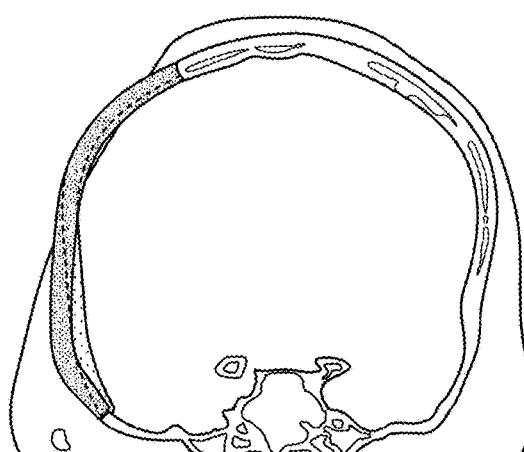
FIG. 7D is a coronal cross-section of the 3D reconstruction of FIG. 7C taken along line 7D thereof, the cross-section showing the configuration of the base portion and the augment portion at a central location of the pterional or temporal region of the skull and face.
Figure 7E:
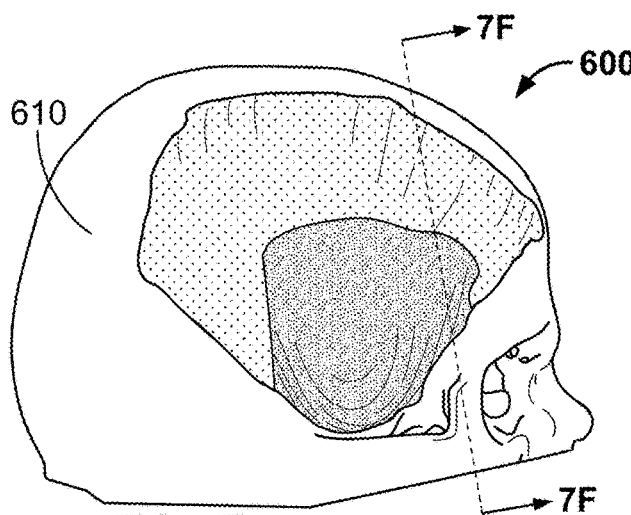
FIG. 7E is yet another lateral view of a 3D reconstruction of the patient-specific cranial implant of FIG. 7A.
Figure 7F:
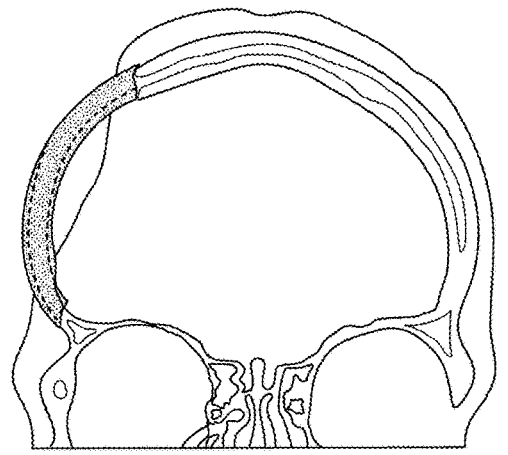
FIG. 7F is a coronal cross-section of the 3D reconstruction of FIG. 7E taken along line 7F thereof, the cross-section showing the configuration of the base portion and the augmented portion at an anterior location of the pterional or temporal region of the skull and face.

FIGS. 7A, 7C, and 7E are a series of lateral views of a 3D reconstruction of one embodiment of an updated implant model 600 implanted in a model of a bone void of a patient's skull and facial bones 610, each of these views including a section line 7B, 7D, and 7F, respectively. Section lines 7B, 7D, and 7F are each situated at different locations on the 3D models. Section line 7B is located in a posterior region, section line 7D is located in a central region, and section line 7F is located in an anterior aspect of the pterional or temporal region of the patient's skull and face 610 in these lateral views. FIGS. 7B, 7D and 7F are coronal cross-sectional views that correspond to FIGS. 7A, 7C and 7E, respectively. Each of these coronal cross-sectional views show updated implant model 600 including a preliminary implant model 700 and an augment portion 800. As can be seen most clearly in FIG. 7D, augment portion 800 is not symmetric to contralateral bone as is preliminary implant model 700. Most of the bulk reproduction of augment portion 800 is created in this central region of the pterion or temporal region of the lateral face.

Figure 8A:
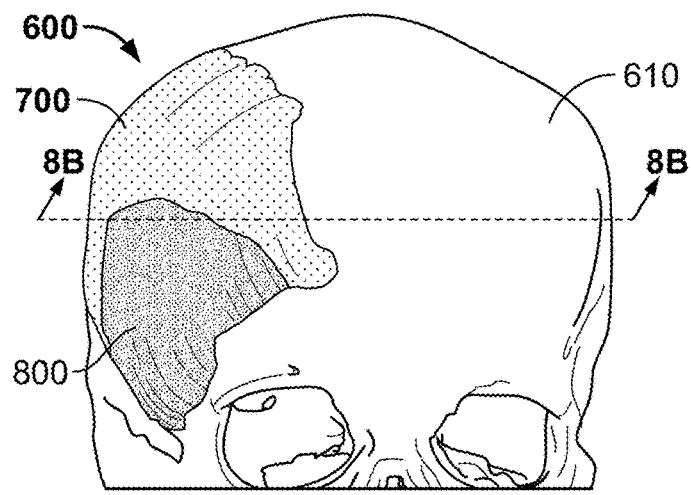
FIG. 8A is a frontal view of a 3D reconstruction of the patient-specific cranial implant shown in FIG. 7A.
Figure 8B:
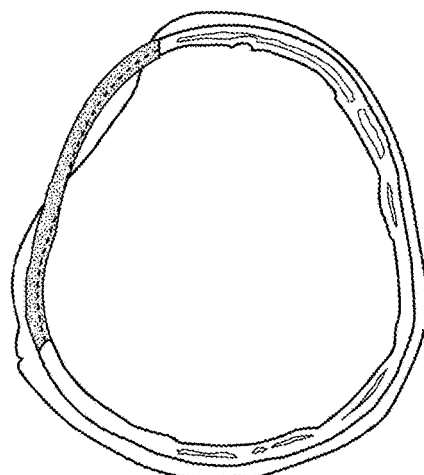
FIG. 8B is an axial cross-section of the 3D reconstruction of FIG. 8A taken along line 8B thereof, the cross-section showing the configuration of the base portion and the augmented portion at a superior location of the pterional or temporal region of the skull and face.
Figure 8C:
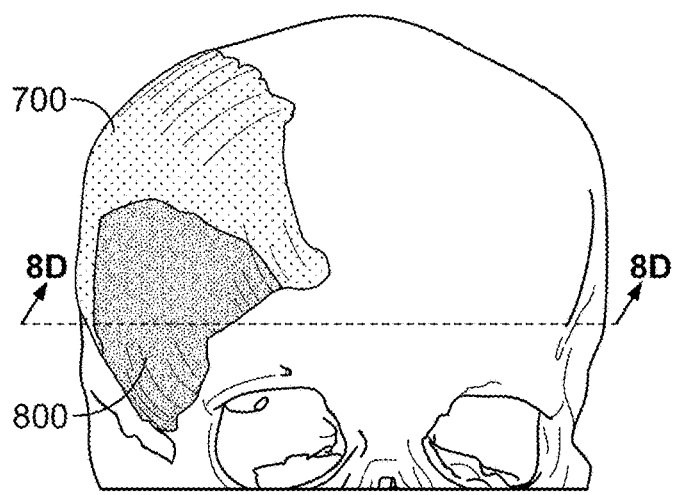
FIG. 8C is another frontal view of a 3D reconstruction of the patient-specific cranial implant of FIG. 7A.
Figure 8D:
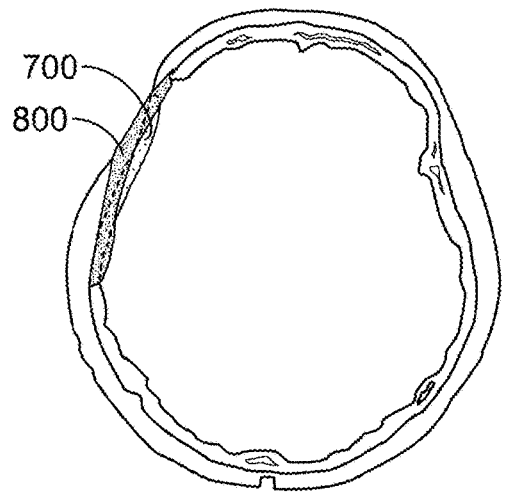
FIG. 8D is an axial cross-section of the 3D reconstruction of FIG. 8C taken along line 8D thereof, the cross-section showing the configuration of the base portion and the augmented portion at a central location of the pterional or temporal region of the skull and face.
Figure 8E:
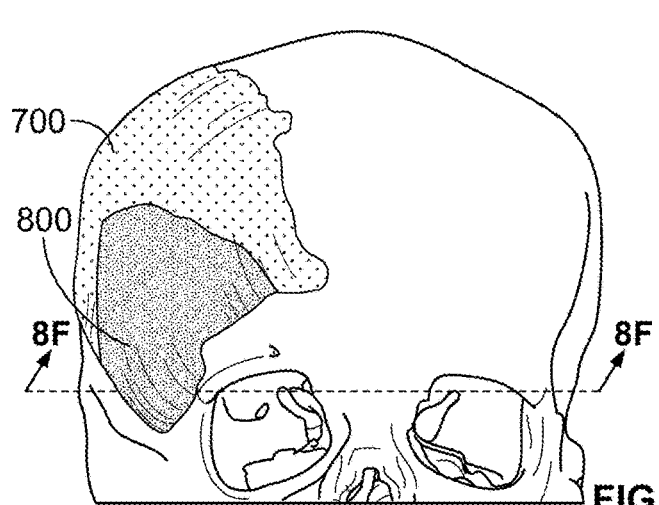
FIG. 8E is yet another frontal view of a 3D reconstruction of the patient-specific cranial implant of FIG. 7A.
Figure 8F:
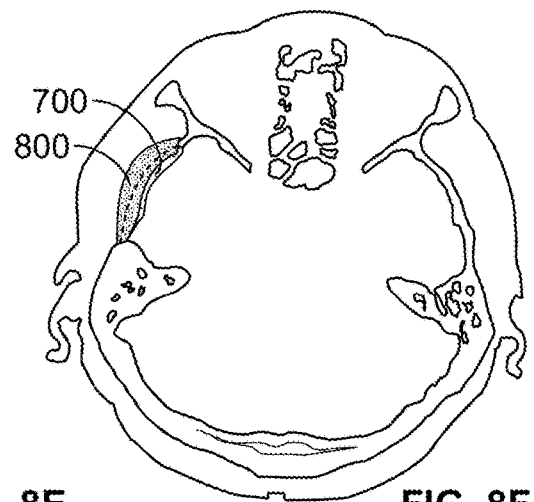
FIG. 8F is an axial cross-section of the 3D reconstruction of FIG. 8E taken along line 8F thereof, the cross-section showing the configuration of the base portion and the augmented portion at an inferior location of the pterional or temporal region of the skull and face.

FIGS. 8A, 8C, and 8E are a series of frontal views of updated implant model 600 each having a section line 8B, 8D, and 8F, respectively. Section lines 8B, 8D, and 8F are each situated at different locations on the 3D models. Section line 8B is located in a superior region, section line 7D is located in a central region, and section line 8F is located in an inferior aspect of the pterional or temporal region of the patient's skull and face in these lateral views. FIGS. 8B, 8D and 8F are axial cross-sectional views that correspond to FIGS. 8A, 8C and 8E, respectively. Each of these axial cross-sectional views shows the difference between preliminary implant model 700 and an updated implant model including augment portion 800. As can be seen most clearly in FIG. 8D, augment portion 800 is not symmetric to contralateral bone as is preliminary implant model 700. It is designed and modified specifically to make up for the soft tissue discrepancy. In other words, it can be used for temporal hollowing deformity prophylaxis and/or secondary correction.

Each patient-specific cranial implant of the present invention will be customized to fit the unique bony void and individual anthropometry of the patient, and therefore, the design inputs described above may be adjusted as needed. For example, with respect to bilateral deficits, the dual-purpose implants can be fabricated used gender-specific anthropometric norms. In addition, in instances of skull tumors or brain tumors invading skull in need of oncological resection (where the actual skull or facial bone defect has yet to be created), these types of dual-purpose implants could be designed using a single-stage approach. For example, if a neurosurgical patient were to present with a large brain and/or skull tumor invading the greater sphenoid wing (the part of the skull located behind the eyeball and part of the orbital skeleton), then resection and reconstruction is quite difficult because, without an exact reconstruction following tumor removal, the eyeball will undoubtedly shift either forward (exophthalmos) or backward (enophthalmos) after the combined tumor resection/reconstruction surgery, and the patient will have a major deformity which is very difficult to fix secondarily. Thus, it would be best for the patient and more desirable to prevent, rather than fix this deformity secondarily). Therefore, instead of using a man-made material in a standard shape (i.e. titanium mesh or porous polyethylene implant with a generic shape)—which is commonly kept "on-the-shelf" in the operating room, exemplary embodiments of the presently described implant provide patient-specific solutions with much better computer-design and a near-exact skull reconstruction. Thus, using exemplary embodiments described herein, the volume of the skull and orbital skeleton have a much better chance of remaining constant and preventing the patient from demonstrating an eyeball-orbital deformity post-op. Once the design of updated implant model 600 is finalized using the CAD software, a patient-specific craniofacial implant may be manufactured using any one of many known manufacturing techniques, such as steriolithography, milling, and molding, for example. The implant can then be manufactured, for example, from alloplastic materials such as PMMA, MEDPOR®, and PEEK, or any other FDA-approved biomaterial.

Referring now to exemplary FIGS. 9A-C, a further exemplary embodiment may be shown and described. Here, an anterior boundary 902 of a pre-existing skull and face 900 defect 901 in need of a customized cranial implant may be shown in FIG. 9A. In this embodiment, however, and unlike previously known cranial implants, there is an extra extension of material 906 that goes above the intact skull and facial bone anteriorly to abut the lateral orbital rim (LOR) and fills in the area around the zygomatico-frontal (ZF) suture 903, as shown in FIG. 9B. This embodiment can reflect a novel method of augmenting the soft tissue deficiency secondary to atrophied muscle and fat following a previous neurosurgical procedure when compared to previous methodologies that only replaced cranial bone defects. A model 904 of a cranial implant may be formed with extension area 906. An exemplary view of the dual-purpose custom cranial implant 908 as implanted can be seen in FIG. 9C.

Figure 10D:
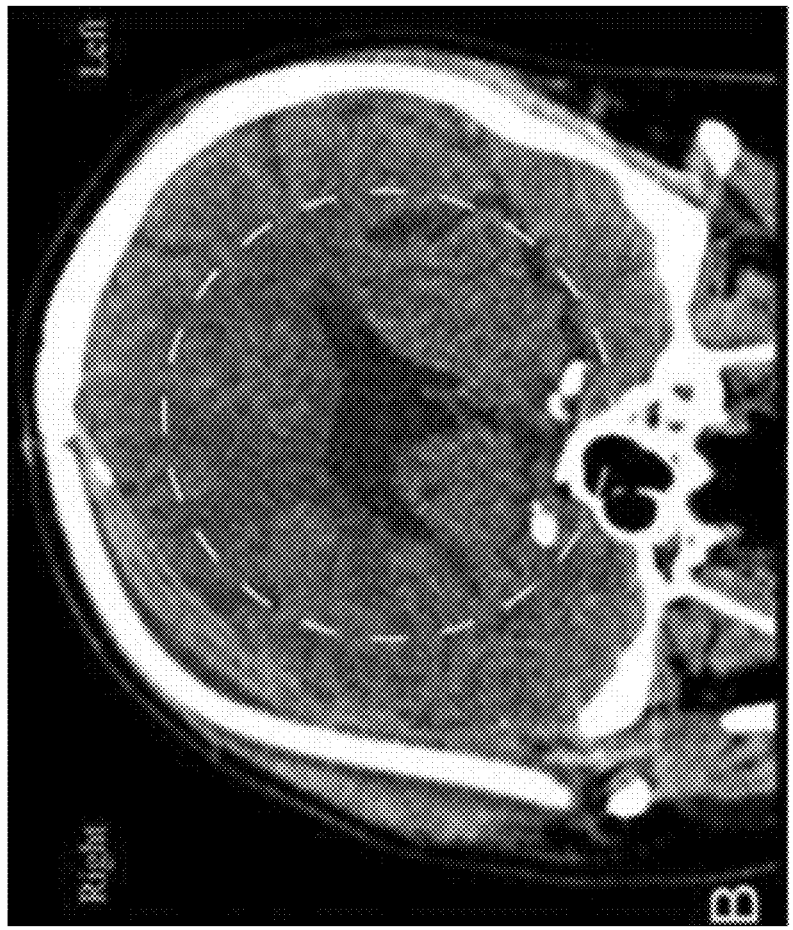
FIG. 10D is an exemplary post operation CT scan showing a cranial implant as implanted.

In still another exemplary embodiment, and referring now to exemplary FIGS. 10A-10C, another custom cranial implant may be shown and described. As seen in FIG. 10A, an inferior boundary 1002 of a pre-existing skull and facial 1000 defect 1001 in need of a customized cranial implant may be shown. The custom cranial implant 1008 in this exemplary embodiment, unlike previous cranial implants, can be designed and have a designated placement position that does not have any planned contact to the left inferior portion of the cranial defect 1001. In other words, the implant can attach to approximately 85%-90% of surrounding bone or bone defect edges (superior, anterior and posterior only), versus previous cranial implants which required attachment to 100% bone defect edges (previous attachment methods and designs included the inferior edge as well). Similar to the above, in FIG. 10B, a model may be formed with an implant 1004 and extension region 1006. Then, and further to this example, the cranial implant 1008 can have a temporal trim window 1010. The temporal trim window 1010 can allow for the "flaring out" of the inferior portion, for example to a consistent, pre-defined lateral projection point 1006 tangential to the plum line of the zygomatic arch (represented as the vertical plum line 1009 in FIG. 10C) "Flaring out" is shown in attached FIG. 10D on the patient's right side to camouflage the soft tissue deficiency, as opposed to the patient's left side—which shows a "tapering in" shape consistent with the contralateral, unaffected temporal bone. This can correct an/or prevent a temporal hollowing deformity along the lateral face and pterional skull region.

Additionally, the implant 1008 as described in this exemplary embodiment, can allow for important space for the temporalis muscle beneath temporal window 1010 to remain below or underneath the custom implant 1008 and temporal trim window 1010 and remain undisturbed, in particular when compared to previously cranial implant designs. In those previous design, the surgeon performing the implant surgery would first mobilize the "scarred in" tissue away from the brain and then reposition it to the outside of the cranial implant or perform resection if devascularized after mobilization. With the present embodiment, the surgeon performing the implant surgery can leave muscle or tissue as-is, or otherwise have it stay the same as the condition it was found in prior to the surgery (assuming no other health risks or anomalies). With the present cranial implant, the surgeon can simply implant the dual-purpose cranial implant above the muscle and utilize contact to the anterior, posterior, and superior bone edges, without need for the inferior edge, which provides numerous benefits. First, it prevents risk of ischemia to the brain if and when new blood vessels (i.e. neoangenesis) formed between the muscle and brain in the interim leading up to secondary cranioplasty surgery. Second, it saves significant operative time, expertise, and effort by the surgeon unlike prior art methods which a surgeon required to perform delicate mobilization. Further, it provides a durable, time-tested, consistent, computer-designed solution to restoring and replacing the missing soft tissue, versus the eventual atrophy and shrinking of temporal tissue when mobilized and affixed to the outside of prior art skull implants. These three exemplary advantages help to minimize surgery-related costs, operative times, and surgical effort—which is a major advance for the specialty. Additionally, this new design result in an extra extension of material that goes above the intact muscle to fill in missing fat and/or muscle but at the same time has a trim window to prevent muscle impingement, pain and/or chewing discomfort. Of note, prior art implant designs did not have extraneous onlay extensions and/or augmented sections for temporal restoration.

Further, exemplary embodiments include the temporal trim window as seen in exemplary FIG. 10C, which allows a surgeon to avoid impingement of the temporalis muscle once left undisturbed, so that there is no or limited pain associated with this cranioplasty procedure. For example, the patient will not experience pain during post-operative chewing. Additionally, as in contrast to previous designs and methods, the temporal trim window makes for a much more durable, time-lasting reconstruction since the man-made biomaterial will hold its shape indefinitely, as opposed to the constant shrinkage of mobilized tissue seen with prior art techniques. Unlike previous implant designs where the surgeon had to mobilize the muscle off the brain and attach it to the outside of the implant, the muscle would typically atrophy over time and the patient would then lose their desired facial symmetry and have a visible deformity after cranial implant surgery (i.e. cranioplasty). In contrast, by leaving the muscle down in its scarred position by way of the present embodiment, and using the augmented/flared cranial implant design, the implant has a long-lasting shape that avoids occurrences of muscle atrophy or otherwise avoids a breakdown like in the mobilized muscle. This is because the material, versus muscle, holds better form with time and, as a result, avoids long term or long-lasting negative effects on the patient.

For example, utilizing exemplary embodiments described herein, after more than 20-50 years, the implant will still have the same desired shape and fitment. When compared with the prior art, this is highly desirable as the prior art methodologies where the mobilized muscle ultimate atrophies and leaves the patient with facial asymmetries and visible deformities known as temporal hollowing or temporal wasting deformities.

In exemplary FIGS. 11A-D, further exemplary embodiments may be shown. In particular, the temporal trim window 1010 can extend along line 1011 from the zygomatic-frontal suture line area 1007 (also known as the "Z-F suture area") to the zygomatic process of the temporal bone 1013. Thus, along line 1011, it can be known and/or determined where to start the temporal trim window 1010. In the exemplary embodiments, the temporal trim window is an additional advancement in the shape and design of customized cranial implants. In previously exemplary embodiments of this implant design, there was excess material used for soft tissue augmentation around the entire inferior portion. However, the present exemplary embodiments provide a better way which can save additional time, reduce a demand for hand-eye artistry in the operating room, and also provide a method to prevent temporalis muscle impingement. In particular, while previous exemplary embodiments had an augmented area within the caudal portion, it's the implant's shape towards the bottom would consistently impinge the temporalis muscle and require intra-operative modification using a hand-held drill (i.e. burr). As such, present embodiments, using a recent advance, is that we can save the entire intra-operative, burr modification process by adding an additional step to the virtual implant design phase using computer-assisted design/modeling (CAD/CAM). The additional step in the implant design process employs a vector line being drawn between the zygomatic process of the temporal bone and the zygomatic-frontal suture of the lateral orbital rim at the very end of the design phase, as a location for material removal. By connecting a virtual line between these two consistent anatomical points, the designer can consistently trim the caudal portion of the augmented implant as to prevent temporalis muscle compression and all related symptoms, such as trismus and/or pain. It has been found that the superior portion (i.e. superior half) of the convex augmented area can be all that is needed to correct and/or prevent the temporal hollowing deformity, and that the inferior portion (i.e. inferior half) may not be needed at all and may be just an additional step in the operating room. Previous exemplary embodiments thus included unneeded operative time (e.g. an extra 30 minutes), additional expense for the drill and drill bit, and further hand-eye coordination with artistic judgement from the surgeon for an ideal result, as opposed the current exemplary embodiments now described which can utilize computer-design modifications.

Figure 13A:
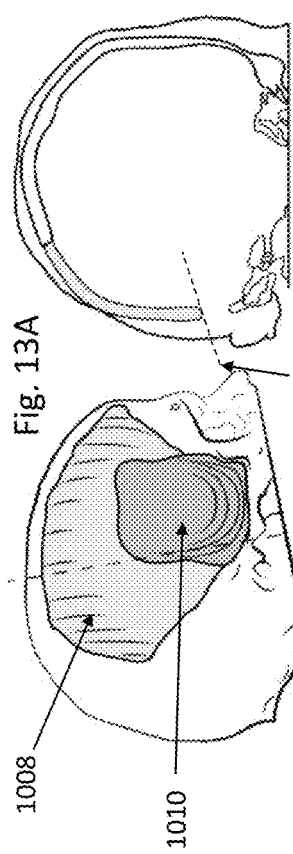
FIG. 13A is an exemplary diagram of a custom cranial implant as implanted.
Figure 13B:
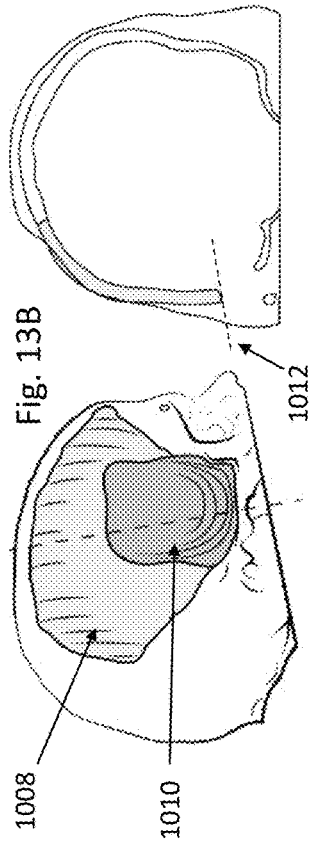
FIG. 13B is an exemplary diagram of a custom cranial implant as implanted.
Figure 13C:
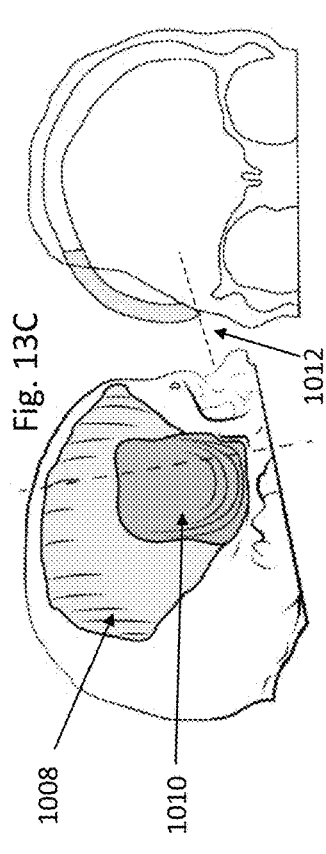
FIG. 13C is an exemplary diagram of a custom cranial implant as implanted.
Figure 12A:
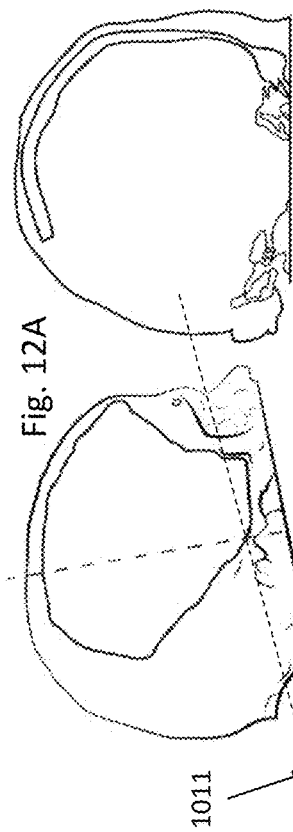
FIG. 12A is an exemplary view of a pre-existing skull and facial defect in need of a customized cranial implant.
Figure 12B:
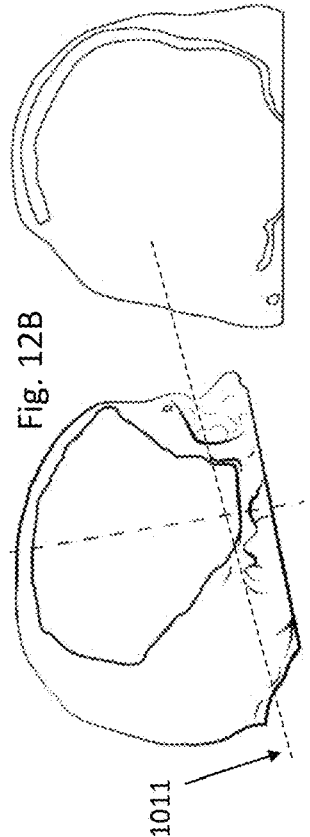
FIG. 12B is an exemplary view of a pre-existing skull and facial defect in need of a customized cranial implant.
Figure 12C:
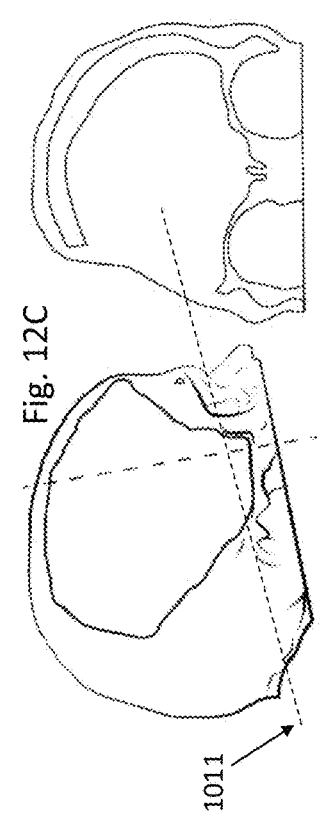
FIG. 12C is an exemplary view of a pre-existing skull and facial defect in need of a customized cranial implant.

Turning now to exemplary FIGS. 12A-C and 13A-C, further exemplary embodiments of a custom cranial implant 1008 with a temporal trim window 1010 may be shown and described. In these exemplary embodiments, the line 1011 in FIGS. 12A-C provides an exemplary before view and line 1012 in FIGS. 13A-C provides an after view where material is removed to make room for undisturbed temporalis muscle scarred down to the brain at the time of a cranial implant. Such exemplary drawings provide further information related to the exemplary embodiments shown previously.

Although the invention herein has been described with reference to particular embodiments, it is to be understood that these embodiments are merely illustrative of the principles and applications of the present invention. It is, therefore, to be understood that numerous modifications may be made to the illustrative embodiments and that other arrangements may be devised without departing from the spirit and scope of the present invention as defined by the appended claims.

What is claimed is:
1. A method of preparing a facial or craniofacial implant for filling a pre-existing bony void following craniectomy in a craniofacial region of a patient and for replacing facial soft tissue as a single-stage reconstruction, comprising:

creating a three-dimensional model of a cranial and/or facial region having a bony void;

based on the three-dimensional model, creating an implant model configured to replace the bony void in the cranial and/or facial region, the implant model further comprising an extension of material that goes above an intact skull region to fill in an area suffering nearby soft tissue atrophy as an onlay extension to prevent and/or correct visible deformity and asymmetry, and forming a temporal trim window on the implant model, wherein the temporal trim window is configured to allow for the temporalis muscle beneath the temporal trim window remain below and undisturbed during the implant surgery.

2. The method of claim 1, wherein the onlay extension is around the zygomatico-frontal suture along the temporal fossa abutting the lateral orbital rim.

* * * * *